United States Patent
Aburub et al.

(10) Patent No.: US 12,071,423 B2
(45) Date of Patent: Aug. 27, 2024

(54) PROCESSES AND INTERMEDIATE FOR THE LARGE-SCALE PREPARATION OF 2,4,6-TRIFLUORO-N-[6-(1-METHYL-PIPERIDINE-4-CARBONYL)-PYRIDIN-2-YL]-BENZAMIDE HEMISUCCINATE, AND PREPARATION OF 2,4,6-TRIFLUORO-N-[6-(1-METHYL-PIPERIDINE-4-CARBONYL)-PYRIDIN-2-YL]-BENZAMIDE ACETATE

(71) Applicant: Eli Lilly and Company, Indianapolis, IN (US)

(72) Inventors: Aktham Aburub, Carmel, IN (US); David Andrew Coates, New Palestine, IN (US); Scott Alan Frank, Indianapolis, IN (US); Mark Steven Kerr, Indianapolis, IN (US); Roger Ryan Rothhaar, Reelsville, IN (US); Radhe Krishan Vaid, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 18/134,747

(22) Filed: Apr. 14, 2023

(65) Prior Publication Data
US 2023/0250076 A1 Aug. 10, 2023

Related U.S. Application Data

(63) Continuation of application No. 17/624,970, filed as application No. PCT/US2020/040881 on Jul. 6, 2020.

(60) Provisional application No. 62/871,965, filed on Jul. 9, 2019.

(51) Int. Cl.
| | | |
|---|---|---|
| *C07D 401/06* | (2006.01) | |
| *A61K 9/20* | (2006.01) | |
| *C07C 51/41* | (2006.01) | |

(52) U.S. Cl.
CPC .......... *C07D 401/06* (2013.01); *A61K 9/2095* (2013.01); *C07C 51/412* (2013.01); *C07B 2200/13* (2013.01)

(58) Field of Classification Search
CPC .. C07D 401/06; A61K 9/2095; C07C 51/412; C07B 2200/13
See application file for complete search history.

(56) References Cited

U.S. PATENT DOCUMENTS

| | | | |
|---|---|---|---|
| 5,011,472 A | 4/1991 | Aebischer et al. | |
| 5,023,252 A | 6/1991 | Hseih | |
| 5,385,912 A | 1/1995 | Neuenschwander et al. | |
| 5,521,196 A | 5/1996 | Audia et al. | |
| 5,521,197 A | 5/1996 | Audia | |
| 5,698,571 A | 12/1997 | Audia et al. | |
| 5,708,008 A | 1/1998 | Audia et al. | |
| 5,708,187 A | 1/1998 | Frlaugh et al. | |
| 5,721,252 A | 2/1998 | Audia et al. | |
| 5,814,653 A | 9/1998 | Flaugh et al. | |
| 5,817,671 A | 10/1998 | Filla et al. | |
| 6,528,529 B1 | 3/2003 | Brann et al. | |
| 6,650,463 B2 | 11/2003 | Obikawa et al. | |
| 6,777,428 B1 | 8/2004 | Krushinski, Jr. et al. | |
| 7,291,632 B2 | 11/2007 | Blanco-Pillado et al. | |
| 7,423,050 B2 | 9/2008 | Cohen et al. | |
| 7,608,629 B2 | 10/2009 | Blanco-Pillado et al. | |
| 7,803,813 B2 | 9/2010 | Blanco-Pillado et al. | |
| 8,044,207 B2 | 10/2011 | Mancuso | |
| 8,697,876 B2 | 4/2014 | Carniaux et al. | |
| 8,748,459 B2 | 6/2014 | Cohen et al. | |
| 2002/0175891 A1 | 11/2002 | Obikawa et al. | |
| 2003/0144285 A1 | 7/2003 | Brann et al. | |
| 2003/0175445 A1 | 9/2003 | Kirsch et al. | |
| 2005/0009871 A1 | 1/2005 | Ramesh et al. | |
| 2005/0080112 A1 | 4/2005 | Madsen et al. | |
| 2005/0222206 A1* | 10/2005 | Cohen ................ | A61K 31/4545 514/318 |
| 2006/0211734 A1 | 9/2006 | Blanco-Pillado et al. | |
| 2007/0129354 A1 | 6/2007 | Aston et al. | |
| 2007/0219187 A1 | 9/2007 | Bessis et al. | |
| 2007/0299110 A1 | 12/2007 | Gagliardi et al. | |
| 2008/0300407 A1 | 12/2008 | Cohen et al. | |
| 2010/0256187 A1 | 10/2010 | Pilgrim et al. | |

(Continued)

FOREIGN PATENT DOCUMENTS

| | | |
|---|---|---|
| EP | 1492786 B1 | 4/2006 |
| EP | 10759491.3 | 7/2018 |

(Continued)

OTHER PUBLICATIONS

Aleksandra Nešić, Jovana Ručić, Milan Gordić, Sanja Ostojić, Darko Micić, Antonije Onjia, Pectin-polyvinylpyrrolidone films: A sustainable approach to the development of biobased packaging materials, Composites Part B: Engineering, vol. 110, 2017, pp. 56-61 (Year: 2017).*
U.S. Appl. No. 18/134,735 filed Apr. 2023, Aktham Aburub.*
U.S. Appl. No. 17/624,970 filed Jan. 2022, Aktham Aburub.*
Remington, "Tablet Ingredients", Remington: The Science and Practice of Pharmacy, 21st Edition, Beringer et al. Editors, 2005, pp. 891-894 (Year: 2005).*
Unit Dose Packaging: A Simple Definition; www.Ifofamerica.com/unit-dose-packaging/unit-dose-packaging-simple-definition/; archived via Wayback Machine on Aug. 11, 2017 (Year: 2017).*
Croscarmellose Sodium; www.drugs.com/inactive/croscarmellose-sodium-204.html; archived via Wayback Machine on Dec. 27, 2011 (Year: 2011).*

(Continued)

*Primary Examiner* — Matthew P Coughlin
*Assistant Examiner* — David M Shim
(74) *Attorney, Agent, or Firm* — Parker D. McCrary; Dan L. Wood

(57) ABSTRACT

The embodiments of present invention provide processes for the large-scale preparation of 2,4,6-trifluoro-N-[6-(1-methylpiperidine-4-carbonyl)-2-pyridyl]benzamide hemisuccinate, and formulations and product forms, such as tablets, made by these processes. Additionally, embodiments of the present invention provide tablets including 25 mg, 50 mg, 100 mg, or 200 mg free base equivalent of 2,4,6-trifluoro-N-[6-(1-methyl-piperidine-4-carbonyl)-pyridin-2-yl]-benzamide hemisuccinate.

4 Claims, 1 Drawing Sheet

(56) References Cited

U.S. PATENT DOCUMENTS

| | | |
|---|---|---|
| 2013/0072524 A1 | 3/2013 | Carniaux et al. |
| 2014/0221385 A1 | 8/2014 | Hansen et al. |

FOREIGN PATENT DOCUMENTS

| | | |
|---|---|---|
| EP | 10759491.3 | 8/2018 |
| EP | 3551617 A1 | 10/2019 |
| EP | 2413933 B2 | 6/2021 |
| JP | 03255426 A | 11/1991 |
| KR | 20060067738 A | 6/2006 |
| WO | 9314201 | 7/1993 |
| WO | 9629075 A1 | 9/1996 |
| WO | 9713512 A1 | 4/1997 |
| WO | 9808502 A1 | 3/1998 |
| WO | 9815545 A1 | 4/1998 |
| WO | 9820875 A1 | 5/1998 |
| WO | 9846570 A1 | 10/1998 |
| WO | 9855115 A1 | 12/1998 |
| WO | 9925348 A1 | 5/1999 |
| WO | 0000487 A1 | 1/2000 |
| WO | 0000490 A2 | 1/2000 |
| WO | 0034266 A1 | 6/2000 |
| WO | 0047559 A2 | 8/2000 |
| WO | 0050426 A2 | 8/2000 |
| WO | 200105763 A2 | 1/2001 |
| WO | 200206196 A1 | 1/2002 |
| WO | 2003000245 A1 | 1/2003 |
| WO | 2003084949 A1 | 10/2003 |
| WO | 04047739 A2 | 6/2004 |
| WO | 2004089874 A1 | 10/2004 |
| WO | 2004099127 A1 | 11/2004 |
| WO | 2005007621 A2 | 1/2005 |
| WO | 2005044797 A1 | 5/2005 |
| WO | 2006048771 A1 | 5/2006 |
| WO | 2006058905 A1 | 6/2006 |
| WO | 2006081127 A2 | 8/2006 |
| WO | 2006108487 A1 | 10/2006 |
| WO | 08114971 A1 | 9/2008 |
| WO | 2010115125 A1 | 10/2010 |
| WO | 2011123654 A1 | 10/2011 |
| WO | 2018010345 A1 | 1/2018 |
| WO | 2018106657 A1 | 6/2018 |
| WO | 2019050759 A1 | 3/2019 |

OTHER PUBLICATIONS

Aleksandra Nešić, Jovana Ružić, Milan Gordić, Sanja Ostojić, Darko Micić, Antonije Onjia, Pectin-polyvinylpyrrolidone films: A sustainable approach to the development of biobased packaging materials, Composites Part B: Engineering, vol. 110, 2017, pp. 56-61 (Year: 2017).*

Rojas, J.; Uribe, Y.; Zuluaga, A. Die Pharmazie—An International Journal of Pharmaceutical Sciences, vol. 67, No. 6, Jun. 2012, pp. 513-517(5) (Year: 2012).*

Sodium Lauryl Sulfate (European Medicines Agency: Sodium laurilsulfate used as an excipient; published Oct. 9, 2017 (Year: 2017).*

Size, Shape, and Other Physical Attributes of Generic Tablets and Capsules Guidance for Industry. U.S. Food and Drug Administration. Center for Drug Evaluation and Research. Jun. 2015, 1-7. (Year: 2015).*

Adham et al., "Cloning of Another Human Serotonin Receptor (5-HT1F): A Fiffth 5-HT1 Receptor Subtype Coupled to the Inhibition of Adenylate Cyclase", Proc. Natl. Acad. Sci. U.S.A., 90:408-412 (1993).

Berge et al. "Pharmaceutical Salts." J. Pharm. Sci 66.1(1977):1-19.

Caira, "Crystalline Polymorphism of Organic Compounds", Topics in Current Chemistry Springer Berlin, DE, vol. 198, Jan. 1, 1998, pp. 163-208.

Cephalalgia 2009, 29, 122-123 "Abstracts of the European Headache and Migraine Trust International Congress 2008, Sep. 4-7, 2008, Abstract PC. 11 of Reuter Entitled COL-144, A Selective 5-HT1F Agonist, for the Treatment of Migraine Attacks" (D4A) and Related Poster (D4B).

Cephalalgia 2009, 29, 122-123 "Abstracts of the European Headache and Migraine Trust International Congress 2008, Sep. 4-7, 2008, Abstract PC. 12 of Nelson Entitled COL-144: Preclinical Profile of a Selective 5-HT1F Receptor Agonist for Migraine" (D3A) and Related Poster (D3B).

Cephalalgia 29 (Suppl. 1) (2009) 24-25 "14th Congress of the International Headache Society Sep. 10-13, 2009, Philidelphia, PA", Abstract PO33 of Liefaard Entitled "Prediction of Therapeutically Effective Dose of OL-144 Based on Relationship Between Plasma Concentrations and Headache Response" (D7A) and Related Poster (D7B).

Cephalalgia 29 (Suppl. 1) (2009) 24-25 "14th Congress of the International Headache Society Sep. 10-13, 2009, Philadelphia, PA", abstract PO34 of Pilgrim entitled "COL-144, an orally bioavailable selective 5-HT1F receptor agonist for acute migraine therapy" (D8a) and related poster (D8b).

Clinical Trial Record NCT00883051 as Stored in the Internet Archive.

Clinical Trials "A Placebo-Controlled Adaptive Treatment Assignment Study of Intravenous COL-144 in the Acute Treatment of Migraine—Study 2 of 2 for search of: Colucid", Clinical Trials, Oct. 4, 2006 (4 pages).

Clinical Trials "Dose-ranging Study of Oral COL-144 in Acute Migraine Treatment—Study 1 of 2 for search of: Colucid", Clinical Trials, Apr. 17, 2009.

Drug Data Report 2009, 31(10), 964.

Emea "Note for guidance on general considerations for clinical trials", Mar. 1998.

Färkkilä, M. et al., "Efficacy and tolerability of lasmiditan, an oral 5-HT1F receptor agonist, for the acute treatment of migraine: a phase 2 randomised, placebo-controlled, parallel-group, dose-ranging study," Lance Neurology 2012, 11(5), 405-413.

Ferrari et al. "Oral Triptans (Serotonin 5-HT1B/1D Agonists) in Acute Migraine Treatment: A Meta-Analysis of 53 Trials." Lancet. 358(2001):1668-1675.

Goadsby et al. "Migraine—Current Understanding and Treatment." N. Engl J. Med. 346.4(2002):257-270.

Goldstein et al. "Selective Seratonin 1F (5-HT1F) Receptor Agonist LY334370 for Acute Migraine: a Randomised Controlled Trial." Lancet. 358.9289(2001):1230-1234.

Graham et al. "Mechanism of Migraine Headache and Action of Ergotamine Tartrate." Arc. Neurol. Pyschaitry. 39.4(1938):737-763.

Gros et al. "Aggregative Activation in Heterocyclic Chemistry. Part 5. Lithiation of Pyrldine and Quinoline With the Complex Base Buli-ME2N(CH2)2OLI (Buli-Lidmae)." J. Chem. Soc., Perkin Trans. 1. 24(1997(:3597-3600.

Hall et al. "A Group Sequential Adaptive Treatment Assignment Design for Proof of Concept and Dose Selection in Headache Trials." Contemp. Clin. Trials. 26.3(2005):349-364.

Headache Classification Subcommittee of the International Headache Society. "The International Classification of Headache Disorders: Second Edition." Cephalalgia. 24.S11(2004):1-160.

Herrick-Davis et al. "Detection and Characterization of the Serotonin 5-HT 1D Receptor in Rat and Human Brain." J. Neurochem. 50.5(1988):1624-1631.

Ho et al. "Efficacy and Tolerability of MK-0974 (Telcagepant), a New Oral Antagonist of Calcitonin Gene-Related Peptide Receptor, Compared With Zolmitriptan for Acute Migraine: a Randomised, Placebo-Controlled, Parallel-Treatment Trial." Lancet. 372. 9656(2008):2115-2123.

Humphrey et al. "Serotonin and Migraine." Ann. N.Y. Acad. Sci. 600(1990):587-598.

Information About Publication Date of Reuter et al. (2009) Cephalalgia, 29(1):101-178.

International Headache Society Clinical Trials Subcommittee. "Guidelines for Controlled Trials of Drugs in Migraine: Second Edition." Cephalalgia. 20.9(2000):765-786.

International Search Report and Written Opinion of the International Searching Authority of PCT/US2020/040881 (filed on Jul. 6, 2020 by Eli Lilly and Company); international search completed on Oct. 20, 2020; mailed on Oct. 28, 2020; 8 pages.

King, F. D., "Bioisosteres, Conformational Restriction, and Pro-Drugs—Case History: An Example of a Conformational Restriction

(56) References Cited

OTHER PUBLICATIONS

Approach", in Medicinal Chemistry: Principles and Practice, Royal Society of Chemistry, Cambridge, England, Ch. 14, pp. 206-209 (1994).

Maassenvandenbrink et al. "Coronary Side-Effect Potential of Current and Prospective Antimigraine Drugs." Circulation. 98.1(1998):25-30.

Moskowitz. "Interpreting Vessel Diameter Changes in Vascular Headaches." Cephalalgia. 12.1(1992):5-7.

Moskowitz. "Neurogenic Inflammation in the Pathophysiology and Treatment of Migraine." Neurol. 43.S3(1993):S6-S20.

Nelson et al. COL-144: Preclinical Profile of a Selective 5-HT1F Receptor Agonist for Migraine. Cephalalgia. 29(2009):122-123. (Abstract # PC. 12).

Olesen et al. "Calcitonin Gene-Related Peptide Receptor Antagonist BIBN 4096 BS for the Acute Treatment of Migraine." N. Engl. J. Med. 350.11(2004):11404-1110.

Phebus et al., "Characterization of LY344864 as a Pharmacological Tool to Study 5-HT1F Receptors: Binding Affinities, Brain Penetration and Activity in the Neurogenic Dural Inflammational Model of Migraine", Life Sciences, 6(21), 2117-2126 (1997) (Abstract Only).

Press Release of Colucid Pharmaceuticals Inc. entitled "Phase II Results of col. 144 Presented at European Headache and Migraine Trust International Congress 2008", Sep. 6, 2008.

Radl et al., "Synthesis and Antinociceptive Activity of Some 3-Chlorophenyl- and 6-Chloro-2-Pyridinyl Derivatives", Coll. Czech. Che,. Comm., 64(2):377-388 (1999) (Abstract Only).

Reuter et al., "COL-144: A Selective 5-HTIF Agonist for the Treatment of Migraine Attacks" Cephalalgia, vol. 29, Jan. 2009.

Schoonman et al. "Migraine Headache is Not Associated With Cerebral of Meningeal Vasodilation—A 3 T Magnetic Resonance Angioraphy Study." Brain. 131.PT8(2008):2192-2200.

Stovner et al. "The Global Burden of Headache: a Documentation of Headache Prevalence and Disability Worldwide." Cephalalgia. 27.3(2007)193-210.

Streitwieser et al. (Eds), "Metalation." Introduction to Organic Chemistry, Upper Saddle River, NJ: Prentice Hall. (1992):1011-1012.

U.S. National Library of Medicine, "Dose-ranging Study of Oral col. 144 in Acute Migraine Treatment" Apr. 17, 2009.

Visser et al. "Chest Symptoms After Sumatriptan: a Two-Year Clinical Practice Review in 735 Consecutive Migraine Patients." Cephalalgia. 16.8(1996):554-559.

Weinshank et al. "Human Serotonin 1D Receptor is Encoded by a Subfamily of Two Distinct Genes: 5-HT1DA and 5-HT1DB." PNAS. 89.8(1992):3630-3634.

Welch et al. "Tolerability of Sumatriptan: Clinical Trials and Post-Marketing Experience." Cephalalgia. 20.8(2000):687-695.

WHO Drug Information, vol. 23, No. 4, 2009, 322-323.

Zhang, et al, Discovery of Selective N-[3=(1-Methyl-Piperdine-4-Carbonyl)-Phenyl]-Benzamide-Based 5-HTIF Receptor Agonists: Evolution From Bicyclic to Monocyclic Cores, Bioorganic & Medicinal Chemistry Letters, 25 (2015) 4337-4341.

Farkkita, et al, "Efficacy and Tolerability of Lasmiditan, an Oral 5-HT1F Receptor Agonist, for the Acute Treatment of Migraine: A Phase 2 Randomised, Placebo-Controlled, Parallel-Group, Dose-Ranging Study", Lancet Neurol, vol. 11, May 2012 405-413.

Goadsby, et al., Phase 3 randomized, placebo-controlled, double-blind study of Lasmiditan for acute treatment of migraine, Brain, a Journal of Neurology, May 27, 2019: 142; pp. 1894-1904.

Sun, et al., Why 90% of clinical drug development fails and how to improve it?, Acta Pharmaceutica Sinica B, 2022:12(7):3049-3062.

* cited by examiner

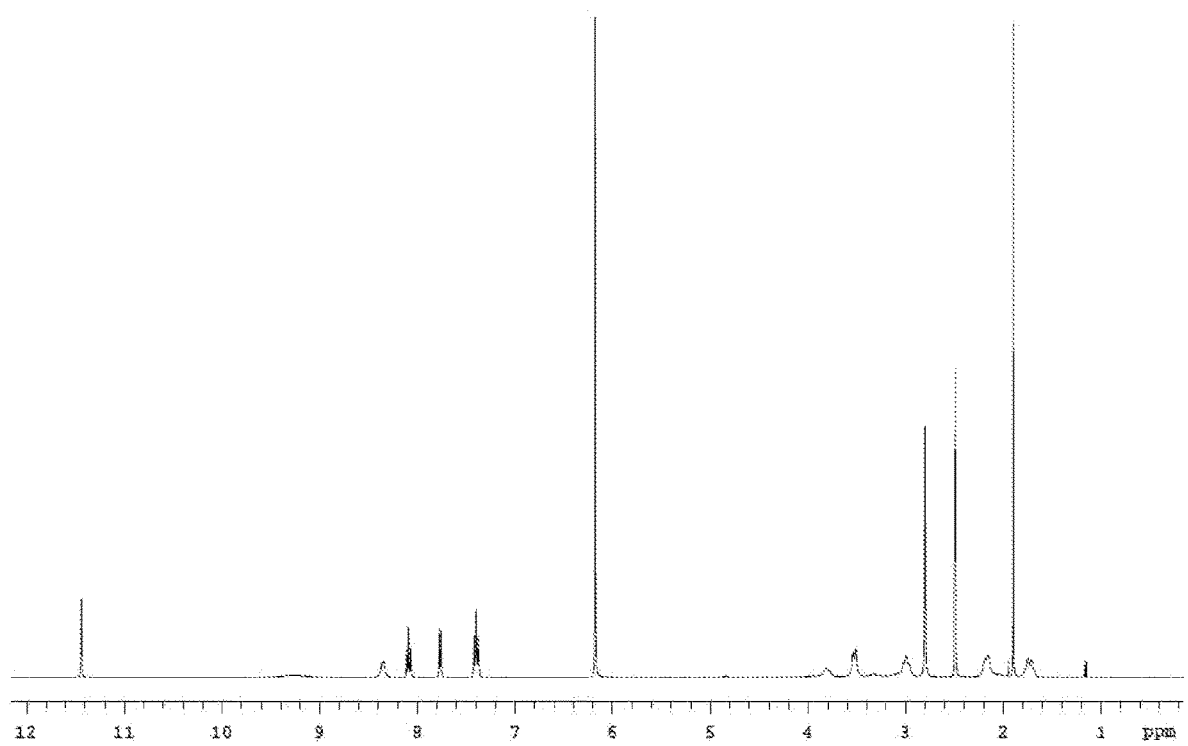

PROCESSES AND INTERMEDIATE FOR THE LARGE-SCALE PREPARATION OF 2,4,6-TRIFLUORO-N-[6-(1-METHYL-PIPERIDINE-4-CARBONYL)-PYRIDIN-2-YL]-BENZAMIDE HEMISUCCINATE, AND PREPARATION OF 2,4,6-TRIFLUORO-N-[6-(1-METHYL-PIPERIDINE-4-CARBONYL)-PYRIDIN-2-YL]-BENZAMIDE ACETATE

The embodiments of the present invention relate to the fields of pharmaceutical chemistry and synthetic organic chemistry, and provide processes and an intermediate for the large-scale synthesis of 2,4,6-trifluoro-N-[6-(1-methyl-piperidine-4-carbonyl)-pyridin-2-yl]-benzamide hemi-succinate salt, a 5-HT1F receptor agonist, and formulations and product forms made by these processes, and to preparation of 2,4,6-trifluoro-N-[6-(1-methyl-piperidine-4-carbonyl)-pyridin-2-yl]-benzamide acetate and uses thereof for parenteral formulations and treatment of migraine.

Lasmiditan is a selective and highly potent 5-HT$_{1F}$ receptor agonist which is now approved in the United States, as 50 mg or 100 mg tablets, for acute on-demand treatment of migraine (See e.g. Rubio-Beltrán et al., Pharmacol Ther 2018; 186:88-97, and Lasmiditan for the Treatment of Migraine, Capi, M. et al., Expert Opinion Investigational Drugs, (2017), Vol. 26, NO. 2, 227-234). Lasmiditan (COL 144, LY 573144, CAS Registry No. 439239-90-4) can be described chemically as 2,4,6-trifluoro-N-[6-(1-methyl-piperidin-4-ylcarbonyl)-pyridin-2-yl]-benzamide. U.S. Pat. No. 7,423,050 and U.S. Publication No. 20080300407 describe the hemisuccinate salt of 2,4,6-trifluoro-N-[6-(1-methyl-piperidine-4-carbonyl)-pyridin-2-yl]-benzamide having the structural formula:

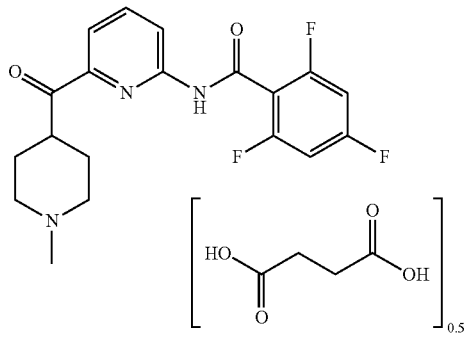

Methods of preparing lasmiditan and salts and certain polymorphic forms, formulations, and dosage forms thereof, are known to the skilled artisan, and are described for example in WO 2003/084949, WO 2011/123654, and WO 2018/106657.

As used herein, useful forms of lasmiditan include pharmaceutically acceptable salts thereof, including but not limited to 2,4,6-trifluoro-N-[6-(1-methyl-piperidin-4-ylcarbonyl)-pyridin-2-yl]-benzamide mono-hydrochloride salt, and 2,4,6-trifluoro-N-[6-(1-methyl-piperidine-4-carbonyl)-pyridin-2-yl]-benzamide hemi-succinate salt. A synthetic route for the preparation of the hemi-succinate salt of 2,4,6-trifluoro-N-[6-(1-methyl-piperidine-4-carbonyl)-pyridin-2-yl]-benzamide has been disclosed previously as shown below in Scheme A. The overall yield of lasmiditan starting with commercially available piperidine 4-carboxylic acid via the route described in Scheme A below is about 10-46% over all 9 steps. Improvements in the synthesis of lasmiditan could provide substantial and varied benefits, particularly for production at large-scale.

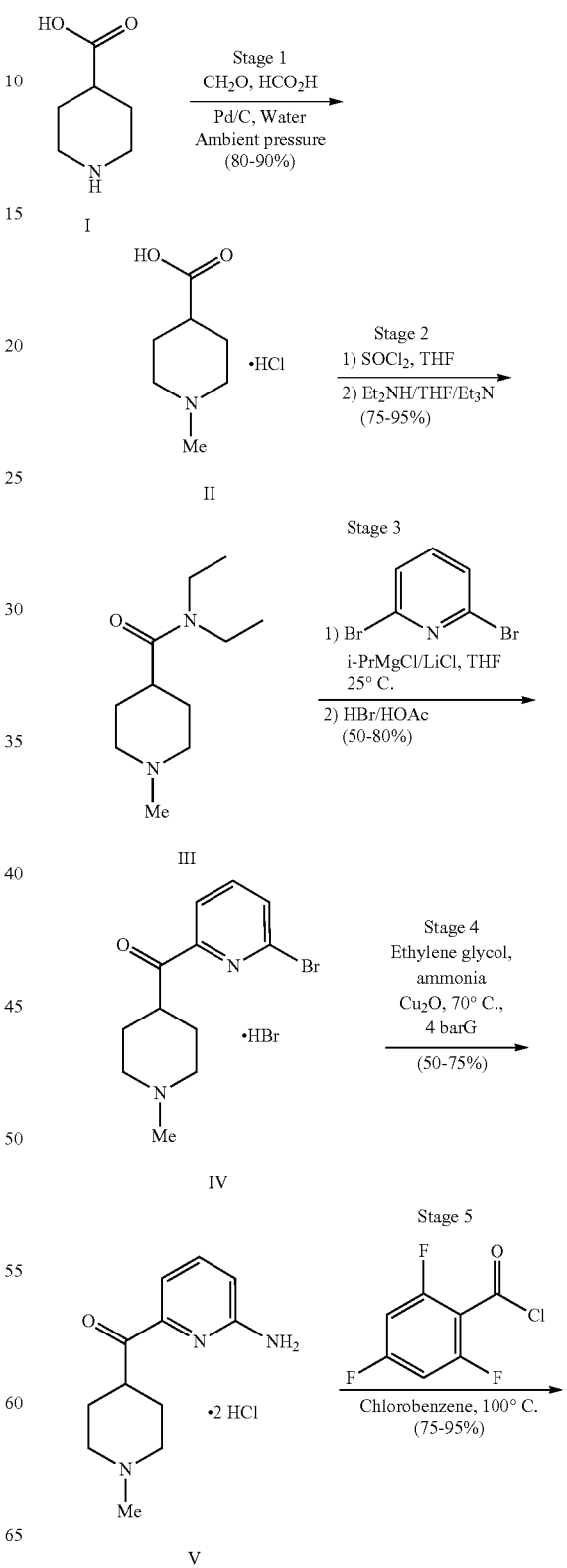

Scheme A

-continued

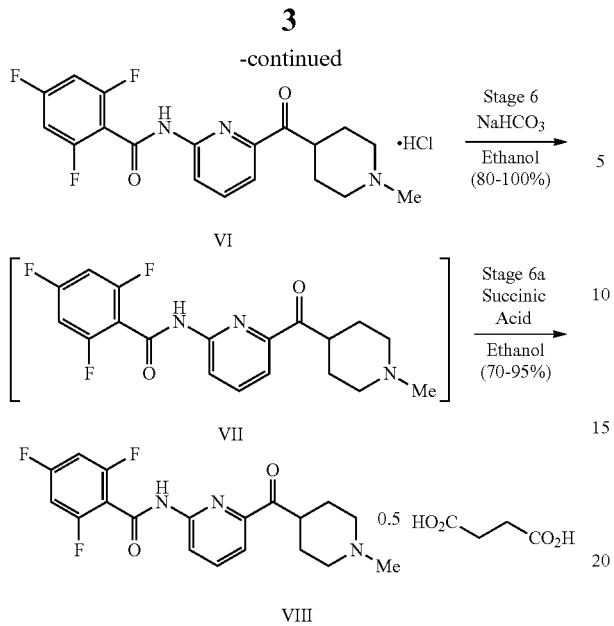

Synthetic chemistry process routes may be redesigned or revised aiming to achieve various advantages, including for example: improved yields, obtaining crystalline products, decreasing impurity profiles, utilizing commercially available intermediates, minimizing the number of synthetic steps needed, reducing the inputs required and/or the by-products produced, or any useful combination of such improvements, to achieve important real-world outcomes including decreased costs, providing less resource intensive processes, and facilitating efficient production. Improved methods of making lasmiditan are needed which may achieve one or more of these aims, particularly for large-scale synthesis.

Further, migraine is one of the most common presenting symptoms in emergency rooms. Current methods for headache relief in the emergency room setting, when using lasmiditan for patients who have difficulty administering a tablet due to nausea and/or vomiting, may need to rely on the preparation of a diluted formulation of about 1 mg/ml lasmiditan delivered intravenously over an extended period of time, for example from about 20-60 minutes. Lasmiditan has been delivered intravenously in clinical studies in doses from about 1-60 mg delivered in 60 ml infusions over 20 minutes (See US Patent Application Publication No. 2010/0256187). The safe and effective treatment of migraine with lasmiditan for patients unable to administer tablets would be enabled by the availability of a high concentration parenteral dosage form. The present disclosure also addresses this need.

SUMMARY

The embodiments of the present invention provide processes for the preparation of lasmiditan hemisuccinate, 2,4,6-trifluoro-N-[6-(1-methylpiperidine-4-carbonyl)-2-pyridyl]benzamide hemisuccinate salt, and/or compositions thereof, and/or particularly useful intermediates for use in these processes. The embodiments of the present invention further provide for the preparation of lasmiditan acetate, 2,4,6-trifluoro-N-[6-(1-methylpiperidine-4-carbonyl)-2-pyridyl]benzamide acetate salt, and/or compositions thereof, and/or uses of lasmiditan acetate, and formulations thereof, in subcutaneous drug delivery.

In one embodiment, referred to as Route I, the present invention provides a process for preparing a compound of the formula:

comprising the steps of:
i.) Treatment of piperidine-4-carboxylic acid under reductive amination conditions comprising formaldehyde and formic acid in water with subsequent treatment with aqueous HCl followed by water distillation and acetonitrile addition, with repeated dilution/distillation until the water content is not more than 0.2% by Karl-Fischer analysis, to obtain solid 1-methylpiperidine-4-carboxylic acid hydrochloride;

ii.) Treatment of 1-methylpiperidine-4-carboxylic acid hydrochloride with a chlorinating agent such as thionyl chloride in chlorobenzene obtain 1-methylpiperidine-4-carboxylic acid chloride;

iii.) Treatment of 1-methylpiperidine-4-carboxylic acid chloride with N,N-diethylamine in chlorobenzene containing triethylamine with subsequent base wash and subsequent treatment with aqueous HCl in isopropanol to obtain solid N,N-diethyl-1-methyl-piperidine-4-carboxamide hydrate hydrochloride;

iv.) Treatment of N,N-diethyl-1-methyl-piperidine-4-carboxamide hydrate hydrochloride with a mineral base such as aqueous NaOH in a non-polar solvent such as methyl-tert-butyl ether with subsequent water wash, phase separation, and distillation of the organic solvent until the water content is not more than 0.1 weight % by Karl Fischer analysis to obtain N,N-diethyl-1-methyl-piperidine-4-carboxamide;

v.) Subsequent treatment of N,N-diethyl-1-methyl-piperidine-4-carboxamide with (6-bromo-2-pyridyl)lithium in a non-polar organic solvent such as methyl-tert-butyl ether with subsequent extraction of the resulting mixture with water and a suitable organic solvent such as n-butanol, phase separation, and repeated distillation of the organic solvent until the water content is not more than 0.2 weight % by Karl-Fischer analysis, to obtain (6-bromo-2-pyridyl)-(1-methyl-4-piperidyl)methanone;

vi.) Treatment of (6-bromo-2-pyridyl)-(1-methyl-4-piperidyl)methanone with aqueous HBr and subsequent extraction with n-butanol followed by repeated distillation of the organic solvent until the water content is not more than 0.3% by Karl-Fischer analysis, to obtain solid (6-bromo-2-pyridyl)-(1-methyl-4-piperidyl)methanone hydrobromide;

vii.) Treatment of (6-bromo-2-pyridyl-1-methyl-4-piperidyl)methanone hydrobromide with a solution of $NH_3$ in ethylene glycol in the presence of $Cu_2O$ catalyst at about 80° C. for about 2 hr, with subsequent washes with water, saturated aqueous NaCl, and 20% aqueous NaOH and subsequent extraction with a non-polar aprotic solvent such as methyl-tert-butyl ether, phase separation, and treatment of the organic phase with 5 weight % carbon;

viii.) Filtration of the above mixture, dilution with a suitable polar alcoholic solvent such as isopropanol, and repeated distillation of the organic solvent until the water content is not more than 0.2% by Karl-Fischer analysis, with subsequent treatment of the resulting residue with isopropanol, water, and 20 weight % HCl, wherein the water concentration of the resulting slurry is at least 2%, filtration of the resulting slurry, and drying under vacuum at 40° C. for 16-24 hr to obtain (6-amino-2-pyridyl)-(1-methyl-4-piperidyl)methanone dihydrate dihydrochloride;

ix.) Treatment of (6-amino-2-pyridyl)-(1-methyl-4-piperidyl)methanone dihydrate dihydrochloride in chlorobenzene with 6 weight/weight % NaOH in water at about 54° C. for about 30 min, with subsequent phase separation and vacuum distillation of the aqueous solution to obtain (6-amino-2-pyridyl)-(1-methyl-4-piperidyl)methanone;

x.) Subsequent treatment of (6-amino-2-pyridyl)-(1-methyl-4-piperidyl)methanone with 2,4,6-trifluorobenzoic acid chloride in chlorobenzene at about 100° C. for about 4 hr, with subsequent cooling, charging with acetonitrile and heating the resulting slurry to 80° C. for about 1 hr, and subsequent collection of the resulting solid by filtration, to obtain solid 2,4,6-trifluoro-N-[6-(1-methylpiperidine-4-carbonyl)-2-pyridyl]benzamide hydrochloride;

xi.) Treatment of 2,4,6-trifluoro-N-[6-(1-methylpiperidine-4-carbonyl)-2-pyridyl]benzamide hydrochloride with saturated aqueous Na$_2$CO$_3$ in methyl-tert-butyl ether;

xii.) Treatment of the mixture of step xi above with SiO$_2$ with subsequent filtration, treatment with carbon, filtration, and evaporation, dilution with ethanol, and distillation until the water content is not more than 1% by Karl-Fischer analysis, to obtain 2,4,6-trifluoro-N-[6-(1-methylpiperidine-4-carbonyl)-2-pyridyl]benzamide;

xiii.) Treatment of 2,4,6-trifluoro-N-[6-(1-methylpiperidine-4-carbonyl)-2-pyridyl]benzamide in ethanol with a solution of 0.5 equivalents succinic acid in ethanol at about 55° C. for not less than 3 hr at RT, and subsequent collection of the solid by filtration, to obtain solid 2,4,6-trifluoro-N-[6-(1-methylpiperidine-4-carbonyl)-2-pyridyl]benzamide hemisuccinate.

In the process of Route I above, preferably the reactions are performed using batch processing methodology. In an embodiment the batches by Route I are produced at process scale. In an embodiment the batches by Route I are produced in at least 1 kilogram. In an embodiment the batches by Route I are produced in at least 10 kilograms. In an embodiment the batches by Route I are produced in at least 100 kilograms.

In the process of Route I above, the use of chlorobenzene avoids degradation which occurs under alternative methods, such as THF, which reacts with the acid chloride under scale (e.g., 100 kg) resulting in essentially no yield of the acid chloride.

In another embodiment, referred to as Route II, the present invention provides a process for preparing a compound of the formula:

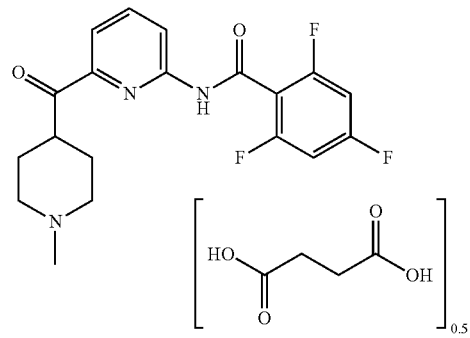

comprising the steps of:

i.) Treatment of piperidine-4-carboxylic acid under reductive amination conditions comprising formaldehyde and formic acid in water with subsequent treatment with aqueous HCl followed by water distillation and acetonitrile addition, with repeated dilution/distillation until the water content is not more than 0.2% by Karl-Fischer analysis, to obtain solid 1-methylpiperidine-4-carboxylic acid hydrochloride;

ii.) Treatment of 1-methylpiperidine-4-carboxylic acid hydrochloride with a chlorinating agent such as thionyl chloride in chlorobenzene to obtain 1-methylpiperidine-4-carboxylic acid chloride;

iii.) Treatment of 1-methylpiperidine-4-carboxylic acid chloride with N,N-diethylamine in chlorobenzene containing triethylamine with subsequent base wash and subsequent treatment with aqueous HCl in isopropanol to obtain solid N,N-diethyl-1-methyl-piperidine-4-carboxamide hydrate hydrochloride;

iv.) Treatment of N,N-diethyl-1-methyl-piperidine-4-carboxamide hydrate hydrochloride with a mineral base such as aqueous NaOH in a non-polar solvent such as methyl-tert-butyl ether with subsequent water wash, phase separation, and distillation of the organic solvent until the water content is not more than 0.1 weight % by Karl Fischer analysis to obtain N,N-diethyl-1-methyl-piperidine-4-carboxamide;

v.) Subsequent treatment of N,N-diethyl-1-methyl-piperidine-4-carboxamide with (6-bromo-2-pyridyl)lithium in a non-polar organic solvent such as methyl-tert-butyl ether with subsequent extraction of the resulting mixture with water and a suitable organic solvent such as n-butanol, phase separation, and repeated distillation of the organic solvent until the water content is not more than 0.2 weight % by Karl-Fischer analysis, to obtain (6-bromo-2-pyridyl)-(1-methyl-4-piperidyl)methanone;

vi.) Treatment of (6-bromo-2-pyridyl)-(1-methyl-4-piperidyl)methanone with aqueous HBr and subsequent extraction with n-butanol followed by repeated distillation of the organic solvent until the water content is not more than 0.3% by Karl-Fischer analysis, to obtain solid (6-bromo-2-pyridyl)-(1-methyl-4-piperidyl)methanone hydrobromide;

vii.) Treatment of (6-bromo-2-pyridyl-1-methyl-4-piperidyl)methanone hydrobromide in a biphasic mixture of water and toluene with solid KOH for about 3 hr with subsequent separation of the organic layer and evaporation of the solvent to obtain of (6-bromo-2-pyridyl-1-methyl-4-piperidyl)methanone;

viii.) Treatment of (6-bromo-2-pyridyl-1-methyl-4-piperidyl)methanone with 2,4,6-trifluorobenzamide in toluene containing K₂CO₃, water, Pd(OAc)₂, and Xantphos at about 70° C. for about 12 hr, until the (6-bromo-2-pyridyl)-(1-methyl-4-piperidyl)methanone content is not more than 0.1% by HPLC, with subsequent dilution of the reaction mixture with water and EtOAc, subsequent treatment with thiourea-modified silica gel at 60° C. for about 8 hr, with subsequent filtration to obtain a solution of 2,4,6-trifluoro-N-[6-(1-methylpiperidine-4-carbonyl)-2-pyridyl]benzamide;

ix.) Treatment of a solution of 2,4,6-trifluoro-N-[6-(1-methylpiperidine-4-carbonyl)-2-pyridyl]benzamide in EtOAc with a solution of about 0.5 equivalents of succinic acid dissolved in EtOH at 55° C. for about 3 hr, with subsequent cooling to RT over about 10 hr, and collection of the resulting solids by filtration, to obtain solid 2,4,6-trifluoro-N-[6-(1-methylpiperidine-4-carbonyl)-2-pyridyl]benzamide hemisuccinate.

In the process of Route II above, preferably the reactions are performed using batch processing methodology. In an embodiment the batches by Route II are produced at process scale. In an embodiment the batches by Route II are produced in at least 1 kilogram. In an embodiment the batches by Route II are produced in at least 10 kilograms. In an embodiment the batches by Route II are produced in at least 100 kilograms.

In the process of Route II above, the use of chlorobenzene avoids degradation which occurs under alternative methods, such as THF, which reacts with the acid chloride under scale (e.g. 100 kg) resulting in essentially no yield of the acid chloride.

In another embodiment the present invention provides:

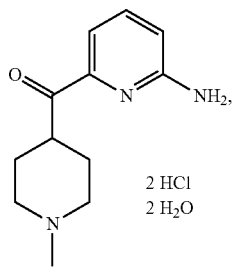 [SMILES: CN1CCC(C(=O)c2cccc(N)n2)CC1 ; "2 HCl2 H2O"]

which can be named as (6-amino-2-pyridyl)-(1-methyl-4-piperidyl)methanone dihydrate dihydrochloride. Preferably this compound is crystalline. (6-amino-2-pyridyl)-(1-methyl-4-piperidyl)methanone dihydrate dihydrochloride is particularly useful in the preparation of 2,4,6-trifluoro-N-[6-(1-methylpiperidine-4-carbonyl)-2-pyridyl]benzamide hemisuccinate, and processes which employ (6-amino-2-pyridyl)-(1-methyl-4-piperidyl)methanone dihydrate dihydrochloride may provide advantageous process characteristics, including but not limited to the purity of intermediate and/or final materials. (6-amino-2-pyridyl)-(1-methyl-4-piperidyl)methanone dihydrate dihydrochloride is believed to be a new stable hydrated form of 6-amino-2-pyridyl)-(1-methyl-4-piperidyl)methanone. The process to isolate (6-amino-2-pyridyl)-(1-methyl-4-piperidyl)methanone dihydrate dihydrochloride described herein provides improved impurity rejection and an improved controlled crystallization process. Form and chemical stability studies showed (6-amino-2-pyridyl)-(1-methyl-4-piperidyl)methanone dihydrate dihydrochloride is generally stable, and drying studies show that over-drying to remove water of hydration is difficult, even under forcing conditions. Use of this intermediate provides advantageously high purity product at expected yield.

In another embodiment the present disclosure provides lasmiditan acetate, which can be represented by the formula:

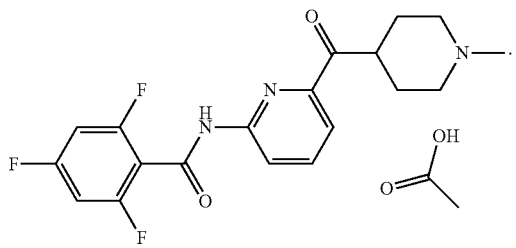

In another embodiment the invention provides lasmiditan acetate in crystalline form, and further provides lasmiditan acetate in crystalline form characterized by an X-ray powder diffraction pattern using CuKα radiation having an intense peak at diffraction angle 2-theta of 26.2° in combination with one or more of the peaks selected from the group consisting of 20.4°, 14.0°, and 17.9° (±0.2° respectively). In another embodiment the present invention provides a pharmaceutical composition comprising lasmiditan acetate according to the above embodiments with one or more pharmaceutically acceptable carriers, diluents, or excipients. Preferably the pharmaceutical composition comprises acetic acid. Preferably the pharmaceutical composition comprises acetic acid and is for subcutaneous administration.

In another embodiment the invention provides a method of treating migraine in a patient comprising administering to a patient in need of such treatment an effective amount of lasmiditan acetate. In another embodiment the invention provides a method of treating migraine in a patient comprising administering to a patient in need of such treatment an effective amount of lasmiditan acetate with one or more pharmaceutically acceptable carriers, diluents, or excipients. In another embodiment the invention provides a method of treating migraine in a patient comprising administering to a patient in need of such treatment an effective amount of lasmiditan acetate with one or more pharmaceutically acceptable carriers, diluents, or excipients wherein the composition comprises acetic acid.

In another embodiment the invention provides lasmiditan acetate for use in therapy. In another embodiment the invention provides a pharmaceutical composition of lasmiditan acetate with one or more pharmaceutically acceptable carriers, diluents, or excipients for use in therapy. In another embodiment the invention provides a pharmaceutical composition of lasmiditan acetate with one or more pharmaceutically acceptable carriers, diluents, or excipients, wherein the composition comprises acetic acid for use in therapy.

In another embodiment the invention provides lasmiditan acetate for use in the treatment of migraine. In another embodiment the invention provides a pharmaceutical composition of lasmiditan acetate with one or more pharmaceutically acceptable carriers, diluents, or excipients for use in the treatment of migraine. In another embodiment the invention provides a pharmaceutical composition of lasmiditan acetate with one or more pharmaceutically acceptable carriers, diluents, or excipients, wherein the composition comprises acetic acid for use in the treatment of migraine.

In another embodiment the present disclosure provides lasmiditan acetate, and pharmaceutical compositions comprising a high concentration of lasmiditan acetate, e.g., about 10-200 mg/ml free base equivalent, in an aqueous carrier. In embodiments, the pharmaceutical composition comprises about 10-200 mg/ml free base equivalent lasmiditan in a buffered aqueous solution. In embodiments, the buffered aqueous solution is at a pH of between pH 6.0-7.5 at 37° C. In embodiments, the buffered aqueous solution comprises acetic acid.

In addition to an aqueous carrier, preferably sterile, deionized, distilled water, the pharmaceutical compositions described herein may further comprise one or more pharmaceutically acceptable excipients or cosolvents. The term "pharmaceutically acceptable" refers to excipients and cosolvents which are suitable for use in contact with the tissues of human beings without excessive toxicity, irritation, allergic response, or other problem or complication, commensurate with a reasonable benefit/risk ratio. Pharmaceutical compositions and processes for preparing the same are well known in the art (see, e.g., Remington: The Science and Practice of Pharmacy (A. Gennaro, et al., eds., 21st ed., Mack Publishing Co., 2005)).

A pharmaceutical composition of lasmiditan acetate can be provided in bulk or in dosage unit form. It is especially advantageous to formulate pharmaceutical compositions of lasmiditan acetate in dosage unit form for ease of administration and uniformity of dosage. The term "dosage unit form" as used herein refers to physically discrete units suitable as unitary dosages for the subject to be treated; each unit containing a predetermined quantity of active compound lasmiditan calculated to produce the desired therapeutic effect in association with the required pharmaceutical carrier. A dosage unit form can be, e.g., an ampoule, a vial, or a syringe.

In embodiments, the disclosure provides a pharmaceutical composition comprising an amount of lasmiditan acetate as described herein wherein the amount is from 10 mg to 200 mg per dose. In embodiments, the disclosure provides a pharmaceutical composition comprising an amount of lasmiditan acetate as described herein wherein the amount is 10 mg, 20 mg, 30 mg, 40 mg, 50 mg, 100 mg, or 200 mg per dose. The forgoing doses are based on an adult human of average weight. Smaller doses would be acceptable for individuals of lighter weight, for example the elderly or children. Therefore, in embodiments, the pharmaceutical composition may comprise a smaller dose, such as 5, 10, or 15 mg.

As described herein, the highly concentrated aqueous solutions of lasmiditan acetate enables the administration of a single therapeutically effective dose by injection of a high concentration aqueous solution of lasmiditan, for example, by an intravenous, subcutaneous, or intramuscular route.

In embodiments, the disclosure provides high concentration aqueous solutions of lasmiditan acetate. In embodiments, the high concentration aqueous solution of lasmiditan acetate is formulated as a parenteral dosage form. In embodiments, the high concentration aqueous solution contains 10-200 mg/ml free base equivalent of lasmiditan. In embodiments, the high concentration aqueous solution of lasmiditan acetate is in the form of a parenteral dosage form. In embodiments, the parenteral dosage form is a buffered aqueous solution of 10-200 mg/ml free base equivalent of lasmiditan. In embodiments, the parenteral dosage form is a buffered aqueous solution of 10, 20, 30, 40, 50, 100 or 200 mg/ml free base equivalent of lasmiditan. In embodiments, the parenteral dosage form is suitable for subcutaneous or intramuscular injection. Preferably the parenteral dosage form is for subcutaneous injection. In embodiments, the pH of the buffered solution is between pH 6.0-7.5 at 37° C.

In embodiments, the buffered aqueous solution comprises a buffering system based on an organic acid. In embodiments, the organic acid is a di- or tri-carboxylic acid. In embodiments, the di- or tri-carboxylic acid is selected from the group consisting of acetic acid and citric acid. In embodiments, the organic acid is succinic acid. In embodiments, the buffer is an acetic acid buffer. In embodiments, the buffered aqueous solution is free of organic solvents. In embodiments, the buffered aqueous solution is free of organic solvents and surfactants. In a preferred embodiment the buffered aqueous solution comprises lasmiditan acetate, and acetic acid, and sodium hydroxide, adjusted to pH between 6.0-7.5 at 37° C.

In embodiments, the parenteral dosage form of lasmiditan acetate is provided in the form of a pre-filled syringe suitable for administration by a subcutaneous route. In embodiments, the pre-filled syringe comprises 10-50 mg/ml free base equivalent of lasmiditan. In embodiments, the pre-filled syringe comprises 10, 20, 30, 40, 50 or 100 mg/ml free base equivalent of lasmiditan. In embodiments, the lasmiditan is provided in a buffered aqueous solution having a pH 6.0-7.5 at 37° C. In embodiments, the pre-filled syringe is suitable for at-home use, for example, for those migraine sufferers who might face an extreme and rapid onset of headache. In embodiments, the pre-filled syringe is contained in a package with instructions for parenteral administration, preferably by subcutaneous injection. In embodiments, the pre-filled syringe is in the form of an autoinjector with instructions for subcutaneous injection.

In embodiments, the parenteral dosage form of lasmiditan acetate is provided in the form of a vial containing 10-50 mg/ml free base equivalent of lasmiditan. In embodiments, the parenteral dosage form of lasmiditan acetate is provided in the form of a vial containing 10, 20, 30, 40, 50 or 100 mg/ml free base equivalent of lasmiditan. In embodiments, the lasmiditan is provided in a buffered aqueous solution having a pH 6.0-7.5 at 37° C.

The disclosure also provides methods for acute treatment of migraine headache attacks, the methods comprising administering a therapeutically effective dose of lasmiditan acetate as described herein. In embodiments, the parenteral solution is administered by subcutaneous injection. In embodiments, the parenteral solution comprises 10-50 mg/ml free base equivalent of lasmiditan acetate in a buffered aqueous solution at pH 6.0-7.5 at 37° C. In embodiments, the parenteral solution comprises 10, 20, 30, 40, 50 or 100 mg/ml free base equivalent of lasmiditan. In embodiments, the methods comprise administering a single therapeutically effective dose of lasmiditan acetate in a volume of less than or equal to 1 ml, such as from about 0.5 to 1 ml, for example by a single subcutaneous injection. In embodiments, the injection volume is about 1 ml. In embodiments, the injection volume is about 0.5 ml.

The present invention provides a method for the treatment of migraine, in a patient in need thereof, comprising administering to the patient 20-200 mg per subcutaneous dose of lasmiditan acetate and a pharmaceutically acceptable diluent or carrier. The present invention provides a method for treatment of migraine, in a patient in need thereof, comprising administering to the patient 20 mg per subcutaneous dose of lasmiditan acetate and a pharmaceutically acceptable diluent or carrier. The present invention provides a method for the treatment of migraine, in a patient in need thereof, comprising administering to the patient 50 mg per subcutaneous dose of lasmiditan acetate and a pharmaceutically acceptable diluent or carrier. The present invention provides a method for the treatment of migraine, in a patient in need thereof, comprising administering to the patient 75 mg per subcutaneous dose of lasmiditan acetate and a pharmaceutically acceptable diluent or carrier. The present invention provides a method for the treatment of migraine, in a patient in need thereof, comprising administering to the patient 100 mg per subcutaneous dose of lasmiditan acetate and a pharmaceutically acceptable diluent or carrier. The present invention provides a method for the treatment of migraine, in a patient in need thereof, comprising administering to the patient 150 mg per subcutaneous dose of lasmiditan acetate and a pharmaceutically acceptable diluent or carrier. The present invention provides a method for the treatment of migraine, in a patient in need thereof, comprising administering to the patient 200 mg per subcutaneous dose of lasmiditan acetate and a pharmaceutically acceptable diluent or carrier.

In some embodiments, a patient is a human who has been diagnosed as having a condition or disorder in need of prevention with a pharmaceutical composition described herein. In some embodiments, a patient is a human that is characterized as being at risk of a condition or disorder for which administration with a pharmaceutical composition described herein is indicated. In those instances where the disorders which can be treated by the methods of the present invention are known by established and accepted classifications, such as migraine, episodic headache, chronic headache, chronic cluster headaches, and/or episodic cluster headaches, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress. Migraine patients can further be diagnosed with migraine, with or without aura (1.1 and 1.2), as defined by International Headache Society (IHS) International Classification of Headache Disorders, 3rd edition, (ICHD-3) beta version (The International Classification of Headache Disorders, 3rd edition (beta version), Cephalalgia 2013; 33:629-808). In some embodiments, the human patient has been diagnosed with episodic migraine prior to receiving chronic administration of lasmiditan, preferably nightly, to prevent migraine. In some embodiments, the human patient has been diagnosed with chronic migraine prior to receiving the antibody. In some embodiments, the human patient experiences auras with their migraine headaches. In some embodiments, the human patient does not experience auras with their migraine headaches.

As used herein "migraine" includes but is not limited to migraine attacks. As used herein "migraine attack" refers to the following description. Symptoms may overlap within various phases of a migraine attack and not all patients experience the same clinical manifestations. In the prodrome phase, the majority of patients have premonitory symptoms that may precede the headache phase by up to 72 hours. These include changes in mood and activity, irritability, fatigue, food cravings, repetitive yawning, stiff neck, and phonophobia. These symptoms may endure well into the aura, headache, and even postdrome phases. Some patients experience an aura phase, wherein about one-third of patients experience transient neurological deficits during attacks. The ICHD-3 defines aura as 1 or more transient, fully reversible neurological deficits, of which at least 1 has to have a unilateral localization, that develops over 5 minutes or more, and of which each deficit lasts between 5 and 60 minutes. While a visual aura, which may show positive (fortification spectra), negative (scotoma), or both phenomena, is found in over 90% of the cases, and the most common deficit, sensory, motor, speech, brain stem, and retinal aura symptoms may also occur. A transient wave of neuronal depolarization of the cortex is believed to be the pathophysiological brain mechanism underlying the clinical phenomenon of migraine aura. In the headache phase, headache attacks which may last 4 to 72 hours are accompanied by nausea, photophobia and phonophobia, or both. The headache is characterized as unilateral, pulsating, of moderate or severe intensity, and aggravated by physical activity; two of these characteristics suffice to fulfill the diagnostic criteria. In the postdrome phase, characteristic symptoms reflect those observed during the premonitory phase. Typical postdrome symptoms include tiredness, difficulties in concentrating, and neck stiffness. It remains unclear whether these symptoms initiate in the premonitory phase and persist throughout the headache phase into the postdrome phase, if they may also initiate during the headache phase, or even appear after the headache phase has ended.

A "migraine headache" as used herein refers to headache, with or without aura, of ≥30 minutes duration, with both of the following required features (A and B): A) at least 2 of the following headache characteristics: 1) unilateral location, 2) pulsating quality, 3) moderate or severe pain intensity, and 4) aggravation by or causing avoidance of routine physical activity; AND B) during headache at least one of the following: a) nausea and/or vomiting, and/or b) photophobia and phonophobia. A "probable migraine headache" as used herein refers to a headache of greater than 30 minutes duration, with or without aura, but missing one of the migraine features in the International Headache Society ICHD-3 definition.

The term "effective amount" or "therapeutically effective amount" means an amount or dose of lasmiditan acetate in a pharmaceutical composition, such as a total amount administered in an administration, which upon single or multiple dose administration to the patient, provides the desired pharmacological effect in the patient, for example an amount capable of activating 5-HT$_{1F}$ receptors. In a preferred embodiment, "effective amount" means an amount of lasmiditan acetate that upon acute administration is capable of rendering a patient migraine attack free following administration. A "dose" refers to a predetermined quantity of lasmiditan acetate calculated to produce the desired therapeutic effect in a patient. As used herein "mg" refers to milligram. As used herein, doses described in mg, refer to the active pharmaceutical ingredient lasmiditan, as free-base equivalent by mass, for instance a "100 mg" dose, refers to 100 mg of the active pharmaceutical ingredient lasmiditan as free-base equivalent. As used herein, a given dose may be interpreted to describe doses of about the indicated amount, in that doses which are up to 10 percent higher or lower than the indicated dose are likewise contemplated to provide useful regimens in a manner similar to the indicated dose.

BRIEF DESCRIPTION OF THE FIGURES

FIG. 1: Graphical representation of an $^1$H NMR spectrum (400 MHZ, DMSO-$d_6$) of lasmiditan acetate containing maleic acid (internal standard).

DETAILED DESCRIPTION

The reactions described herein may be performed via standard techniques known to the skilled artisan by employing routine glassware or may be performed on pilot and/or production scale in equipment designed for such transformations. Further, each of these reactions described may be executed via either a batch process, or where applicable, a flow reaction methodology. The term "batch process" as used herein refers to a process in which raw materials are combined in a reactor or vessel and product is removed at the end of the reaction.

Additionally, certain intermediates described in the following preparations may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example *"Greene's Protective Groups in Organic Synthesis"*, Fourth Edition, by Peter G. M. Wuts and Theodora W. Greene, John Wiley and Sons, Inc. 2007).

The abbreviations listed below when used herein are defined as follows: "Å" means angstrom or angstroms. "ACN" means acetonitrile. "AcOH" means acetic acid. "Bn" means benzyl; "nBuLi" means n-butyllithium. "CAS No." means Chemical Abstracts Registry number. "DCM" means dichloromethane. "DMF" means N,N-dimethylformamide. "DIPEA" means diisopropylethylamine. "DMSO" means dimethyl sulfoxide (perdeuterated [$d_6$] if used for NMR). "EtOAc" means ethyl acetate. "EtOH" means ethanol or ethyl alcohol. "HBTU" means (2-(1H-bezotriazole-1-yl)-1,1,3,3-tetramethyluronium hexafluorophosphate. "HPLC" means high performance liquid chromatography. "HTRF" means homogeneous time-resolved fluorescence. "hr" or "h" means hour or hours. "IPA" means isopropyl alcohol. "IPC" means in-process control. "LAH" means lithium aluminum hydride. "LCMS" means liquid chromatography mass spectrometry. "LDA" means lithium diisopropylamide. "Me" as a substituent in a structural representation of a compound represents a methyl group. "MeOH" means methanol or methyl alcohol. "min" means minutes. "MS" means mass spectrometry or mass spectrum. "MTBE" means methyl tert-butyl ether. "NMR" means nuclear magnetic resonance. "NMT" means not more than. "OAc" means acetate. "psig" means pounds per square inch gauge. "PyBOP" means (benzotriazol-1-yl-oxytripyrrolidinophosphonium hexafluorophosphate). "RT" means room temperature/ambient temperature. "sec" means second or seconds as a unit of time. "TBS-Cl" means tert-butyldimethylsilyl chloride. "TEA" means triethylamine. "THF" means tetrahydrofuran. "tR" means retention time. "w/w" means weight to weight in a ratio.

Improved routes for the preparation of lasmiditan are provided below as Routes I and/or II, and other additional methods as provided below.

"Pharmaceutically acceptable salts" or "a pharmaceutically acceptable salt" refers to the relatively non-toxic, inorganic and organic salt or salts of the compounds of the present invention. It will be understood by the skilled artisan that compounds of the present invention are capable of forming salts. Some compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

"Process scale" synthesis refers to preparations of 500 mg to 1000 kg, or more of 2,4,6-trifluoro-N-[6-(1-methylpiperidine-4-carbonyl)-2-pyridyl]benzamide hemisuccinate. Preferably "process scale" syntheses are performed under Good Manufacturing Process (GMP) or similar conditions required for commercial production of pharmaceutical products for human consumption. Preferably, "process scale" in the processes of Route I and/or II above, refers to batches produced in at least 1 kilogram, and/or batches produced in at least 10 kilograms, and/or batches produced in at least 100 kilograms.

General Chemistry

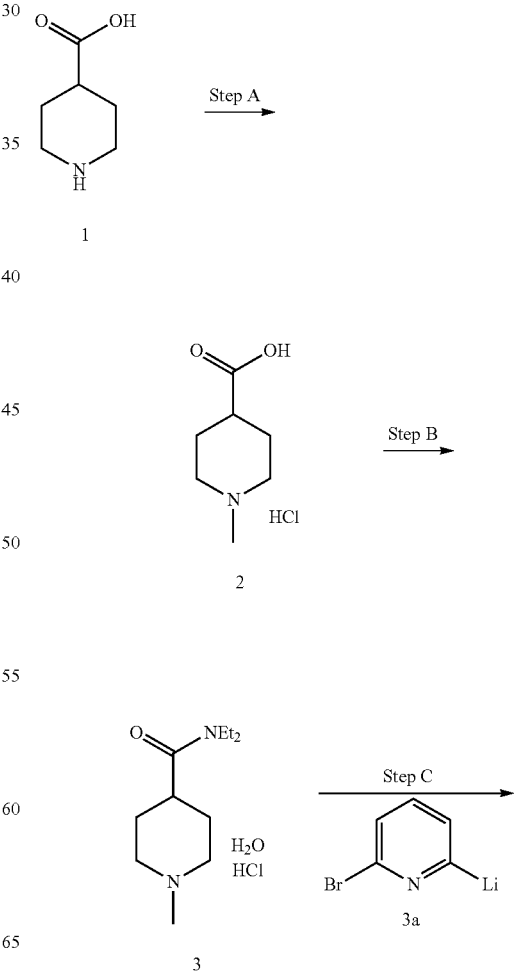

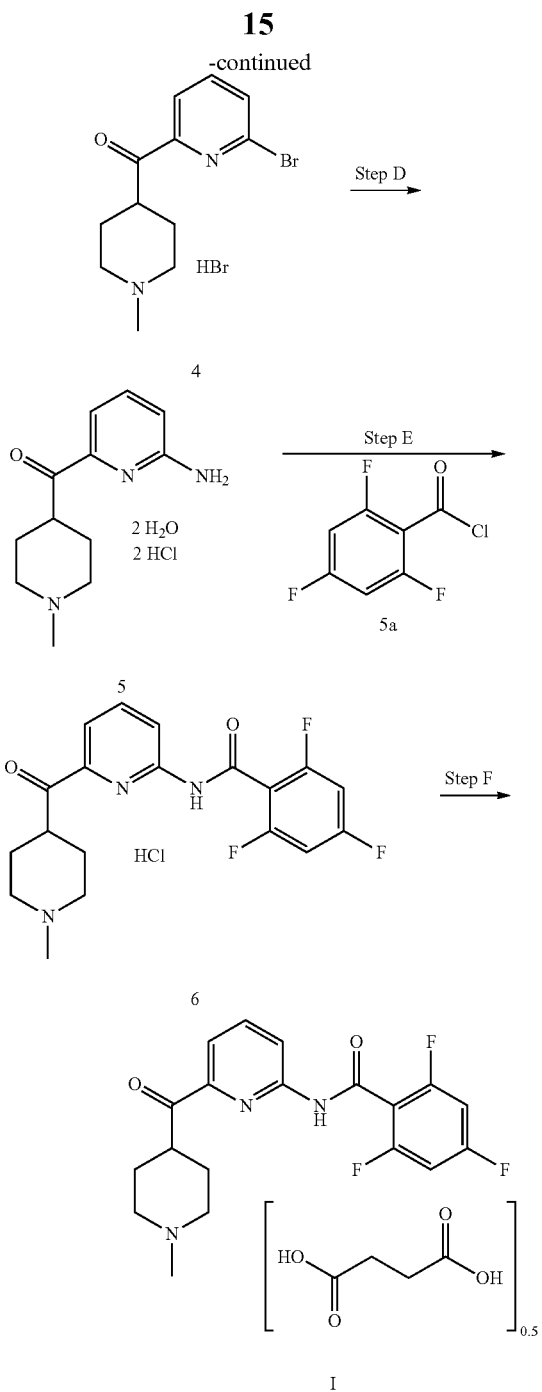

reaction mixture may be cooled to about 0° C. and 1.5 equivalents diethylamine and 3 equivalents trimethylamine added. The free base is stirred with HCl to obtain diethylamide hydrate hydrochloride 3. One skilled in the art will recognize that pyridyl ketone 4 may be obtained by treatment of diethylamide 3 with the lithiated bromopyridine 3a. More specifically, (6-bromo-2-pyridyl)lithium may be formed by treating 2,6 dibromopyridine with n-BuLi at about −58° C. Separately, piperidine-4-diethylamide hydrochloride hydrate 3 may be treated with about 2 equivalents NaOH and the resulting free base added to the lithiated species at about −58° C. The resulting mixture may be treated with HBr to form pyridylbromide hydrobromide 4. Amination of pyridylbromide hydrobromide 4 may be achieved using transition metal catalysis well known to one skilled in the art. More specifically, to pyridylbromide 4 may be added about 0.075 equivalents of $Cu_2O$, about 28 equivalents $NH_3$ in ethylene glycol and stirred to about 80° C. The reaction may be cooled to RT, quenched with $H_2O$, washed with 20% aqueous NaOH, slurried with 20% HCl in IPA and a small amount of $H_2O$, to obtain a aminopyridine dihydrate dihydrochloride 5 as a crystalline solid. Pyridylbenzamide hydrochloride 6 may be prepared by treating the free base of aminopyriyl 5 with the acid chloride 5a. More specifically, aminopyridine dehydrate dihydrochloride 5 may be treated with 6% aqueous NaOH to furnish the free base. Separately, 2,4,6-trifluorobenzoic acid may be treated with thionyl chloride at about 100° C. and the aforementioned freebase of 5, to provide pyridylbenzamide hydrochloride 6. Hemisuccinate I may be created by treating hydrochloride 6 with about 2 equivalents of $NaHCO_3$ followed by about 0.55 equivalents succinic acid to obtain lasmiditan hemisuccinate compound I.

Scheme 2

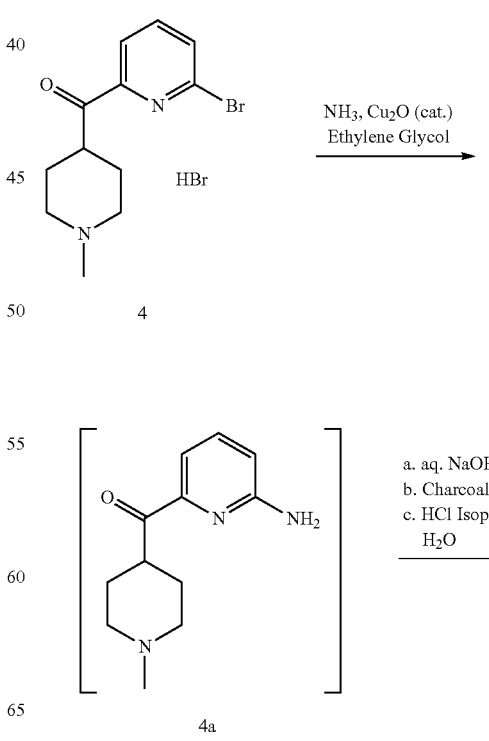

Scheme 1 depicts a process scale synthesis of lasmiditan hemisuccinate compound I. N-Methylation of commercially available piperidine 4-carboxylic acid 1 may be accomplished under various reductive conditions recognizable to the skilled artisan, specifically treatment of the secondary amine with about 1.3 equivalents of formaldehyde in an excess of formic acid, to obtain the N-methylpiperidine 2. Formation of diethylamide 3 may be achieved using conventional amide coupling reagents such as benzotriazole, HBTU or PyBOP or by converting the carboxylic acid to the acid chloride, using reagents well known in the art such as oxalyl chloride or thionyl chloride. More specifically, N-methylpiperidine-4-carboxylic acid 2 may be converted to the acid chloride by treatment with about 1.2 equivalents of thionyl chloride at about 50° C. for 1 hr, at which time the

17

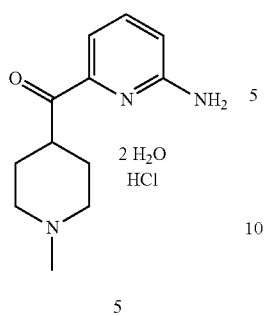

5

18

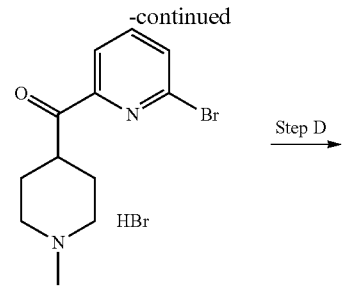

4

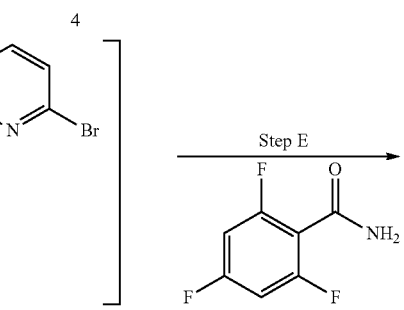

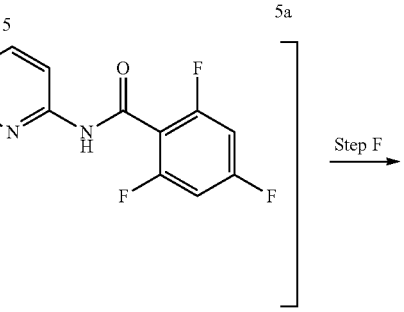

6

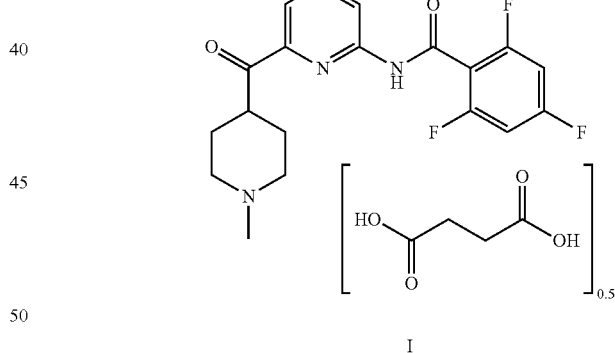

I

Scheme 2 depicts the synthesis of (6-amino-2-pyridyl)-(1-methyl-4-piperidyl)methanone dihydrate hydrochloride 5. Amination of pyridylbromide hydrobromide 4 may be achieved as outlined in scheme 1 using transition metal catalysis well known to one skilled in the art. More specifically, to pyridylbromide 4 may be added about 0.075 equivalents of $Cu_2O$, about 28 equivalents $NH_3$ in ethylene glycol and stirred at about 80° C. The reaction may be cooled to RT, quenched with $H_2O$, washed with 20% aqueous NaOH, slurried with 20% HCl in IPA and a small amount of $H_2O$, to obtain aminopyridine dihydrate hydrochloride 5.

Scheme 3

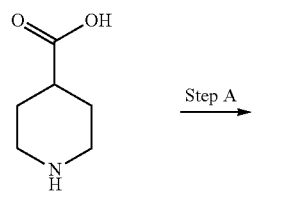

1

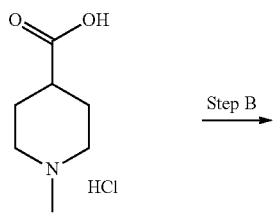

2

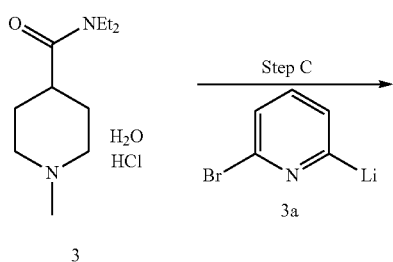

3

Scheme 3 illustrates a modified process synthesis to lasmiditan hemisuccinate I. N-Methylation of commercially available piperidine 4-carboxylic acid 1 may be accomplished under various reductive conditions recognizable to the skilled artisan, specifically treatment of the secondary amine with about 1.3 equivalents of formadehyde in an excess of formic acid, to obtain the N-methylpiperidine 2. Formation of diethylamide 3 may be achieved using conventional amide coupling reagents such as benzotriazole, HBTU or PyBOP or by converting the carboxylic acid to the acid chloride, using reagents well known in the art such as oxalyl chloride or thionyl chloride. More specifically, N-methylpiperidine-4-carboxylic acid 2 may be converted to the acid chloride by treatment with about 1.2 equivalents of thionyl chloride at about 50° C. for 1 hr, at which time the reaction mixture may be cooled to about 0° C. and 1.5 equivalents diethylamine and 3 equivalents trimethylamine added. The free base is stirred with HCl to obtain diethylamide hydrate hydrochloride 3. One skilled in the art will recognize that pyridyl ketone 4 may be obtained by treatment of diethylamide 3 with the lithiated bromopyridine 3a. More specifically, (6-bromo-2-pyridyl)lithium may be formed by treating 2,6 dibromopyridine with n-BuLi at about −58° C. Separately, piperidine-4-diethylamide hydrochloride hydrate 3 may be treated with about 2 equivalents NaOH and the resulting free base added to the lithiated species at about −58° C. The resulting mixture may be treated with HBr to form pyridylbromide hydrobromide 4. Amination of pyridylbromide hydrobromide 4 to obtain amide 6 may be achieved using transition metal catalysis well known to one skilled in the art. Specifically, the pyridyl ketone 4 may be sprung to its corresponding free base form with a suitable mineral base and subjected to Buchwald-type coupling conditions, as is well known in the literature. More specifically, the free base of compound 4 may be stirred in a suitable aprotic solvent, such as toluene or xylene, containing a mixture of about 1-5 weight % water, about 1.1 equivalents commercially available 2,4,6-trifluorbenzamide (CAS #82019-50-9), about 1.5 equivalents of potassium carbonate, about 0.005 to about 0.015 equivalents of a suitable palladium catalyst, such as palladium(II) acetate, and about 0.01 to 0.02 equivalents of a suitable phosphine ligand compound, such as Xantphos, XPhos, or DPEPhos. The resulting mixture may be heated at about 70° C. for about 12-24 hr. The reaction mixture may be diluted with a suitable mixture of water and organic solvent, such as DCM or EtOAc, and the organic layer may be treated with an appropriate palladium scavenger, such as thiourea-modified silica gel, for about 8-24 hr at about RT to about 65° C. The resulting mixture may be cooled, filtered, treated with activated charcoal, filtered, and concentrated under reduced pressure. The resulting residue may be dissolved in an appropriate alcoholic solvent, such as ethanol, and treated slowly with a solution of about 0.5 equivalents of succinic acid dissolved in ethanol at about 55° C. The resulting mixture may be cooled to RT over about 10 hr, and the resulting slurry may be slurry-milled by treatment under a series of thermal cycles of heating to 60° C. and cooling back to RT over 4 hr. The resulting solid may be collected by filtration, dried at about 40° C. for about 4 hr, and optionally jet milled, to obtain lasmiditan hemisuccinate I.

Experimental Procedures

The following preparations of process intermediates further illustrate the invention and represent typical syntheses of various compounds. The reagents and starting materials are readily available or may be readily synthesized by one of ordinary skill in the art. It should be understood that the Preparations and Examples are set forth by way of illustration, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1 mm×50 mm, 3.0μ; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 μm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

NMR spectra are performed on a Bruker A VIII HD 400 or 500 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Chloride analysis is performed on an ESA CORONA® Plus instrument equipped with a CORONA® CAD® (charged aerosol detector)-HPLC, Acclaim Trinity P1 (100× 3.0 mm, 3 um), mobile phase: 50 mM ammonium acetate, pH ~5 in ACN.

The compounds described herein can be prepared by general methods known to the skilled artisan or by processes described herein. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well-known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical.

Preparation 1

1-methylpiperidine-4-carboxylic acid hydrochloride

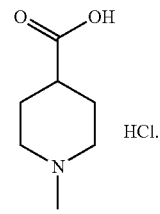

Scheme 1, step A: To a jacketed reactor is charged piperidine-4-carboxylic acid (10.0 g, 77.5 mmol) and deionized water (40 mL). The mixture is heated to reflux (95-100° C.). Formic acid (13.9 g, 302 mmol) is added over 30 min. A 37% aqueous solution of formaldehyde (8.1 g, 101 mmol) is added to the mixture dropwise over at least 30 min. Water (0.3 mL) is used as a line rinse into the reactor. The mixture is stirred for 4 hr at reflux (95-100° C.) and sampled by HPLC for IPC analysis (NMT 0.5% of piperidine-4-carboxylic acid). If the amount of piperidine-4-carboxylic acid is above 0.5%, the mixture is stirred 2 additional hr. If the specification is met, the solution is concentrated under vacuum until ~20 mL of residual volume remains and the residue is cooled to 45-50° C. To the cooled solution is charged 33% aqueous HCl (12.8 g, 116 mmol) over not less than 30 min. Water (0.3 mL) is used as a line rinse into the reactor. Water is distilled off under vacuum until ~20 mL of residual volume remains. To the concentrated solution at 45-50° C. is charged ACN (42.4 mL) and the mixture is concentrated under atmospheric pressure until ~40 mL of residual volume remains. To the concentrated solution at 45-50° C. is charged ACN (20.4 mL) and the mixture is concentrated under atmospheric pressure until ~40 mL of residual volume remains. The dilution/concentration operations are repeated until the in process control for water content by Karl-Fischer analysis is NMT 0.2%; during these operations a slurry forms. To the slurry is charged ACN (10.2 mL) at 45-50° C. The slurry is cooled to 20° C. over 1 h and stirred for an additional 2 h. The resulting solid is isolated by filtration and the cake is rinsed with ACN (10.2 mL). The wet cake is dried at 40° C. under nitrogen at atmospheric pressure to give the title compound (12.1 g, 87% yield). MS (m/z): 144 (M+H).

Preparation 2

N,N-diethyl-1-methyl-piperidine-4-carboxamide hydrate hydrochloride

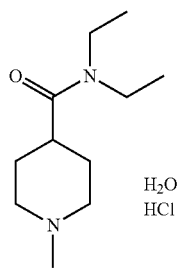

Scheme 1, step B: To a jacketed reactor is charged 1-methylpiperidine-4-carboxylic acid hydrochloride (30.0 g, 167 mmol), chlorobenzene (240 mL) and DMF (0.61 g, 8.35 mmol) and the resulting mixture is heated to 50° C. To the hot suspension is charged thionyl chloride (24.2 g, 200.4 mmol) over a 1 hr period. Chlorobenzene (13.5 mL) is used as a line rinse into the reactor. The mixture is stirred for 5 hr after the completion of the thionyl chloride addition. The solution is then cooled to 0 to 10° C. A solution prepared from diethylamine (17.7 g, 12.5 mmol) and TEA (50.7 g, 25 mmol) is charged to the cold reaction mixture over a 3 hr period. Chlorobenzene (13.5 mL) is used as a line rinse into the reactor. The mixture is stirred for 2 hr after the complete addition of the amine mixture. The reaction is treated with 20 weight % aqueous NaOH (180.3 g, 902 mmol) and stirred at RT for 2 hr. Water (3 mL) is used as a line rinse into the reactor. The mixture is allowed to settle for 2 hr and the aqueous phase is removed. The remaining organic phase is placed under vacuum. The mixture is heated to distill away the residual amines as well as most of the chlorobenzene. The reactor is vented to atmospheric pressure using nitrogen after approximately ten volumes of distillate have been collected. The remaining solution is cooled to between 10° C. to 30° C. THF (120 mL) and water (4.54 g, 252 mmol) are charged to the reactor. With the reaction mixture at RT, the desired product is precipitated by the addition of 20 weight % aqueous HCl in isopropanol (30.4 g, 167 mmol). THF (5.4 mL) is used as a line rinse into the reactor. After the complete addition of HCl, the suspension is stirred for 2 hr at RT. The resulting solid is collected by filtration and washed with THF (75.0 mL). The collected solids are dried under vacuum for 16 hr at 40° C. to give the title compound (35.5 g, 84% yield). MS (m/z): 199 (M+H).

Preparation 3

(6-bromo-2-pyridyl)-(1-methyl-4-piperidyl)methanone hydrobromide

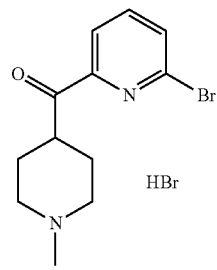 [SMILES: CN1CCC(C(=O)c2cccc(Br)n2)CC1 ; Br]

Scheme 1, step C: A suspension of N,N-diethyl-1-methyl-piperidine-4-carboxamide hydrate hydrochloride (21.5 g, 85.1 mmol) in MTBE (109 mL) is treated with a 20 weight % aqueous solution of NaOH (34.0 g, 170 mmol). A water rinse (1.94 mL) is used to complete the addition. The mixture is stirred at RT for 30 min, the phases are allowed to settle, and phases are separated. The aqueous phase is extracted with MTBE (43.7 mL) and the organic phases combined. The organic phase is dried by distillation at atmospheric pressure until the in process control for water content by Karl-Fischer analysis is <0.10 weight %. If the target analysis is not met, the reaction is charged with MTBE (43.7 mL) and the distillation is repeated. Typically three distillations are required to reach the target analysis for water. In a separate reactor is charged a mixture of 2,6-dibromopyridine (30.2 g, 128 mmol) and MTBE (105 mL) and is cooled to less than −58° C. To the cooled suspension is charged a 2.5M solution of n-BuLi in hexanes (51.3 mL, 128 mmol) over a 2 hr period. A rinse of MTBE (4.5 mL) is used to complete the transfer. The mixture is aged while maintaining the temperature at less than −58° C. for an additional 2 hr after complete n-BuLi addition. After aging, the solution of N,N-diethyl-1-methyl-piperidine-4-carboxamide hydrate hydrochloride in MTBE is added to the cold reaction over a 45 min period. A rinse of MTBE (13.5 mL) is used to complete the transfer. The mixture is aged for at least 30 min after complete addition of N,N-diethyl-1-methyl-piperidine-4-carboxamide hydrate hydrochloride in MTBE. After aging, the reaction is warmed to 0° C. over 1 hr. The cold reaction mixture is added to a 2.5 M aqueous solution of HCl (146 mL, 366 mmol) at a rate to maintain the quench temperature at NMT 30° C. A rinse of MTBE (13.5 mL) is used to complete the transfer. The mixture is stirred for at least 30 min after the transfer is complete and the phases are allowed to settle. The phases are separated and the aqueous phase is retained. n-BuOH (54.8 mL) is added to the aqueous phase and the mixture is treated with a 20 weight % aqueous solution of NaOH (59.5 g, 298 mmol). A rinse of water (2.80 mL) is used to complete the transfer. The mixture is stirred for at least 30 min and the phases are allowed to settle. The phases are separated and the organic phase is retained. The aqueous phase is extracted with n-BuOH (54.8 mL). The combined organic phases are dried by distillation under vacuum to obtain an in process control for water content by Karl-Fischer analysis of <0.20 weight %. If the target analysis is not met, n-BuOH (41.1 mL) is charged and the distillation is repeated. Typically, two distillations are required to reach the in process control target analysis. The concentrated solution is clarified by filtration and a rinse with n-BuOH (89.6 mL) is used to complete the transfer and rinse the filter. The clarified solution is treated with a 48 weight % aqueous solution of HBr (9.91 mL, 87.7 mmol) over a 90 min period. A rinse of n-butanol (13.8 mL) is used to complete the transfer. A check of the pH shows the reaction mixture has a pH ~1. The mixture is dried by distillation at atmospheric pressure to obtain an in process control for water content by Karl-Fischer analysis of <0.30 weight %. The mixture is concentrated to 172 mL. If the target analysis is not met, n-BuOH (54.8 mL) is charged and the distillation is repeated. The mixture is cooled to 20° C. and stirred for 12 hr. The resulting solids are collected by filtration and washed twice with n-BuOH (10.75 mL). The solids are dried under vacuum at 60° C. to obtain the title compound (24.8 g, 80% yield). MS (m/z): 283, 285 ($^{79}$Br, $^{81}$Br, M+H).

Preparation 4

(6-amino-2-pyridyl)-(1-methyl-4-piperidyl)methanone dihydrate dihydrochloride

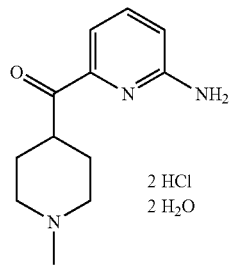 [SMILES: CN1CCC(C(=O)c2cccc(N)n2)CC1 ; "2 HCl2 H2O"]

Scheme 1, step D: To a pressure reactor is charged (6-bromo-2-pyridyl)-(1-methyl-4-piperidyl)methanone hydrobromide (30 g, 82.9 mmol) and Cu$_2$O (880 mg, 6.2 mmol). The headspace is exchanged with nitrogen/vacuum purge cycles three times. To the solids are charged a solution of NH$_3$/ethylene glycol (273.5 g total, 39.1 g NH$_3$, 2.33 mol; 210 mL ethylene glycol) and the resulting mixture is stirred at RT for 2 hr. The mixture is heated to 80° C., stirred for 10 h, and cooled to RT for in process control sampling for (6-bromo-2-pyridyl)-(1-methyl-4-piperidyl)methanone hydrobromide NMT 2%. If the target analysis is not met, the reaction is stirred for another 4 hr at 80° C. and sampled again. To the completed reaction is charged H$_2$O (90 mL) and the mixture is filtered. The filtrate is charged into aqueous NaCl (253.9 g NaCl, 2.73 mol, 13.7 L/kg H$_2$O) and the resulting mixture is stirred at RT for 10 min. To the mixture is charged a 20% aqueous solution of NaOH (4.44 equiv., 368 mmol) and the biphasic mixture is stirred at RT for 5 min. The mixture is extracted with MTBE (90 mL) 4-5 times at RT. The combined MTBE layers are treated with 5 weight % carbon for 30 min and the carbon is removed by filtration. The organic filtrate is concentrated to ~150 mL under vacuum. To the concentrated filtrate is charged IPA (200 mL) and the solution is concentrated to ~150 mL under vacuum two times. The IPA distillations are repeated as needed to meet the target analyses for in process control of water. Water content is confirmed to be not more than 0.2% by Karl-Fischer analysis. In a separate reactor is charged a 20 weight % solution of HCl in IPA (30 g, 166 mmol) and water (10.5 mL) at RT. The concentrated product mixture is charged to the HCl solution over 90 min. The resultant slurry is stirred at RT for not less than 8 hr. The slurry is filtered, rinsed twice with a mixture of 95:5 IPA/H$_2$O (36 mL) at RT, and dried under vacuum at 40° C. for 16-24 hr to afford the title compound (18.4 g 68% yield). MS (m/z): 220 (M+H). $^1$H NMR (400 MHZ, D2O/DMSO-d6) δ ppm 1.74-1.88 (m, 2H), 2.05 (br d, J=14.9 Hz, 2H), 2.73 (s, 3H), 3.01 (td, J=13.1, 2.6 Hz, 2H), 3.41-3.50 (m, 2H), 3.55 (tt, J=12.0, 3.5 Hz, 1H), 7.14 (dd, J=9.0, 0.7 Hz, 1H), 7.59 (d, J=7.2 Hz, 1H), 7.90 (dd, J=9.0, 7.2 Hz, 1H). $^{13}$C NMR (101 MHZ, D2O//DMSO-d6) δ ppm 27.4, 40.7, 44.6, 54.6, 117.2, 121.1, 137.9, 145.2, 156.2, 196.3. Chloride analysis: 20.23% (n=2).

X-Ray Powder Diffraction (XRPD) of Crystalline Forms

The XRPD patterns of crystalline solids are obtained on a Bruker D4 Endeavor X-ray powder diffractometer, equipped with a CuKα source and a Vantec detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

A sample of Preparation 4, (6-amino-2-pyridyl)-(1-methyl-4-piperidyl)methanone dihydrate dihydrochloride, is characterized by an XRD pattern using CuKα radiation as having diffraction peaks (2θ values) as described in Table 1 below, and in particular having peaks at 8.3° in combination with one or more of the peaks selected from the group consisting of 16.6°, 23.5°, and 33.7°, with a tolerance for the diffraction angles of 0.2 degrees.

TABLE 1

X-ray powder diffraction peaks of the crystalline compound of Preparation 4; (6-amino-2-pyridyl)-(1-methyl-4-piperidyl)methanone dihydrate dihydrochloride

| Peak | Angle (° θ) +/− 0.2° | Relative Intensity (% of most intense peak) |
|---|---|---|
| 1 | 8.3 | 100.0% |
| 2 | 16.6 | 49.8% |
| 3 | 19.9 | 8.1% |
| 4 | 22.5 | 15.2% |
| 5 | 23.5 | 25.7% |
| 6 | 25.1 | 17.1% |
| 7 | 28.8 | 11.0% |
| 8 | 29.7 | 17.0% |
| 9 | 30.0 | 13.9% |
| 10 | 33.7 | 23.7% |

Preparation 5

2,4,6-trifluoro-N-[6-(1-methylpiperidine-4-carbonyl)-2-pyridyl]benzamide hydrochloride

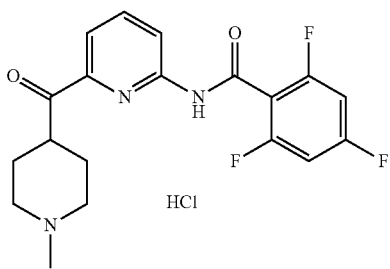 [SMILES: CN1CCC(C(=O)c2cccc(NC(=O)c3c(F)cc(F)cc3F)n2)CC1 ; Cl]

Scheme 1, step E: To a suspension of (6-amino-2-pyridyl)-(1-methyl-4-piperidyl)methanone dihydrochloride dihydrate (10 g, 30.6 mmol) in chlorobenzene (65 mL) is charged 6 w/w % aqueous NaOH (3 g, 75 mmol). The biphasic mixture is heated to 54° C. with stirring for 30 min, the mixture is allowed to separate over 30 min, and the layers are separated at 54° C. The aqueous layer is back-extracted with chlorobenzene (45 mL) at RT. The organic layers are combined and distilled under vacuum to ~62 mL to afford a solution of (6-aminopyridin-2-yl)(1-methylpiperidin-4-yl)methanone. In a separate reactor is charged 2,4,6-trifluorobenzoic acid (5.9 g, 1.1 eq, 33.7 mmol), DMF (62 mg, 0.85 mmol) and chlorobenzene (32 mL) and the mixture is heated to 80° C. To the heated mixture is charged thionyl chloride (4.37 g, 37 mmol) over 4 hr at 80° C. The mixture is stirred at 80° C. for at least 6 hr, and heated to 100° C. for at least 6 hr to purge residual HCl gas. The solution of acid chloride is cooled to RT and transferred to a separate reactor. The acid chloride solution is heated to 100° C. and charged with (6-aminopyridin-2-yl)(1-methylpiperidin-4-yl)methanone over 4 hr. The resulting slurry is agitated for an additional 3 hr at 100° C. and cooled to RT. To the cooled slurry is charged ACN (100 mL). The resulting slurry is heated to 80° C. for 1 hr and cooled to RT over 2 hr. The resulting slurry is further agitated at RT for an additional 1 hr and filtered. The filter cake is washed with ACN (10 mL) at RT. The collected solids are dried under vacuum at 100° C. for 16 hr to obtain the title compound (10.7 g, 85% yield). MS m/z 378 (M+H).

Alternate Procedure For Preparation 5

To a suspension of (6-amino-2-pyridyl)-(1-methyl-4-piperidyl)methanone dihydrochloride dihydrate (10 g, 30.6 mmol) in chlorobenzene (65 mL) is charged 6 w/w % aqueous NaOH (2.97 g, 74.4 mmol). The biphasic mixture is heated to 54° C. with agitation for 30 minutes and the layers are allowed to separate over 30 min. The layers are separated at 54° C. The aqueous layer is back-extracted with chlorobenzene (45 mL) at RT. The organic layers are combined and distilled under vacuum to ~62 mL to afford a solution of (6-aminopyridin-2-yl)(1-methylpiperidin-4-yl)methanone. In a separate reactor is charged 2,4,6-trifluorobenzoic acid (5.9 g, 33.7 mmol), DMF (62 mg, 0.85 mmol) and chlorobenzene (32 mL) and the mixture is heated to 80° C. To the heated mixture is charged thionyl chloride (4.4 g, 37 mmol) over 4 hr at 80° C. The mixture is agitated at 80° C. for at least 6 hours and heated to 100° C. for at least 6 hours to purge residual HCl gas. The solution of acid chloride is cooled to RT and transferred to a separate reactor. The acid chloride solution is heated to 100° C. and to the solution is charged (6-aminopyridin-2-yl)(1-methylpiperidin-4-yl)methanone over 4 hr. The resulting slurry is agitated for an additional 3 hours at 100° C. and cooled to RT. To the cooled slurry is charged ACN (100 mL). The resulting slurry is heated to 80° C. for 1 hr and cooled to RT over 2 hr. The resulting slurry is further agitated at RT for an additional 1 hr and the resulting solids are collected by filtration. The filter cake is washed with ACN (10 mL) at RT. The solids are dried under vacuum at 100° C. for 16 hr to obtain the title compound (10.7 g, 85% yield). MS m/z 378 (M+H).

Preparation 6

2,4,6-trifluoro-N-[6-(1-methylpiperidine-4-carbonyl)-2-pyridyl]benzamide hemisuccinate

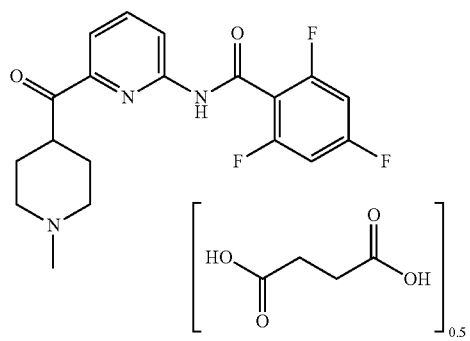

Scheme 1, step F: To a reactor is charged 2,4,6-trifluoro-N-[6-(1-methylpiperidine-4-carbonyl)-2-pyridyl]benzamide hydrochloride (20 g, 48.4 mmol) and MTBE (202 mL). To the stirred slurry at RT is charged a solution of aqueous NaHCO$_3$ (8.13 g, 96.8 mmol NaHCO$_3$ in 200 mL water) over 1 hr. The biphasic mixture is separated and the aqueous layer is back-extracted with MTBE (202 mL). The combined organic layers are distilled under vacuum to a final volume of ~200 mL. To the distilled solution is charged SiO$_2$ (2 g), the resulting mixture is stirred for 30 min at RT, filtered, and the filter cake is rinsed with MTBE (10.8 mL). To the filtrate is charged carbon (340 mg; alternatively, the solution can be filtered through a carbon cartridge) and the resulting mixture is stirred at RT for 30 min and filtered through a 1-5 μm filter, followed by a rinse with MTBE (21.6 mL). The filtrate is distilled under vacuum to ~80 mL. To the concentrated solution is charged ethanol (114 mL) and the resulting solution is distilled under vacuum to ~84 mL. The EtOH add-backs and distillations are continued until the water content is not more than 1% by Karl-Fischer analysis, providing a dry solution of 2,4,6-trifluoro-N-[6-(1-methylpiperidine-4-carbonyl)-2-pyridyl]benzamide. In a separate reactor is charged succinic acid (3.03 g, 25.7 mmol) and EtOH (60 mL). The mixture is stirred and heated at 33° C. until the succinic acid is dissolved completely.

The solution of 2,4,6-trifluoro-N-[6-(1-methylpiperidine-4-carbonyl)-2-pyridyl]benzamide is heated to 55° C. To the heated solution is charged a portion of the solution of succinic acid in EtOH (roughly 1.0 L/kg). The resulting solution is then seeded by the addition of 1 weight % of 2,4,6-trifluoro-N-[6-(1-methylpiperidine-4-carbonyl)-2-pyridyl]benzamide hemisuccinate (200 mg). The resulting slurry is stirred for 30 min and the remainder of the succinic acid in EtOH solution is charged at a constant rate over 2 hr. The reactor contents are stirred for 30 min and cooled to RT, linearly over 2.5 hr. The resulting slurry is stirred at RT for not less than 3 hr. The slurry is filtered and the collected solids are washed with EtOH (60 mL). The solids are dried under vacuum at 45° C. for 16 hr to obtain the title compound (20.4 g, 85% yield). MS m/z 378 (M+H). $^1$H NMR (500 MHZ, DMSO-$d_6$) δ ppm 1.59 (d, J=12.1 Hz, 2H), 1.84 (d, J=12.8 Hz, 2H), 2.08 (t, J=11.4 Hz, 1H), 2.38 (s, 2H), 2.24 (s, 3H), 2.89 (d, J=13.1 Hz, 2H), 3.70 (s, 1H), 7.40 (dd, J=9.4, 7.8 Hz, 2H), 7.75 (d, J=7.6 Hz, 1H), 8.08 (t, J=7.9 Hz, 1H), 8.39 (d, J=8.2 Hz, 1H), 11.47 (s, 1H).

Alternative Procedure For Preparation 6

Scheme 3, Steps D, E and F: To a jacketed reactor is charged (6-bromo-2-pyridyl)-(1-methyl-4-piperidyl)methanone (50 g, 137 mmol,) and toluene (400 mL). Water is added (250 mL), followed by KOH pellets (13.6 g, 206 mmol) and the mixture is stirred for 3 hr at RT. The contents of the reactor are filtered and returned to the reactor. The aqueous layer is drained and if necessary, the organic layer is treated with activated carbon to remove color. The mixture is concentrated at 50° C. and reduced pressure to ~150 mL. Toluene (225 mL) is added back to the reactor under a nitrogen atmosphere and $K_2CO_3$ (28.5 g, 206 mmol), 2,4,6-trifluorobenzamide (26.5 g, 151 mmol), and water (2.5 mL) are added, and the contents are stirred at RT. To a separate flask under a nitrogen atmosphere is charged toluene (20 mL), Pd(OAc)$_2$ (154 mg, 0.68 mmol), and Xantphos (795 mg, 1.37 mmol), and the contents are stirred at RT for 30 minutes. The resulting solution is transferred to the reactor and the reactor is heated to 70° C. with stirring. After 5 hr, the mixture is sampled for IPC HPLC analysis of NMT 0.1% (6-bromo-2-pyridyl)-(1-methyl-4-piperidyl)methanone. If the amount of (6-bromo-2-pyridyl)-(1-methyl-4-piperidyl)methanone is not met, the mixture is stirred 5 additional hr and sampled again. If the IPC is met, the mixture is stirred for an additional 12 hours at 70° C. The contents of the reactor are then cooled to 45° C. Water (250 mL) and EtOAc (250 mL) are added and the mixture is stirred for 1 hr. The agitation is stopped, and the layers are allowed to separate. The aqueous layer is removed and discarded. Water (250 mL) is charged and the resulting mixture is stirred for 1 hr. Agitation is stopped and the layers are allowed to separate. The aqueous layer is removed and discarded. Thiourea-modified silica gel (5 g) is charged and the reactor is heated to 60° C. for 8 hr with stirring. The contents of the reactor are cooled to RT. The solution is filtered and returned to the reactor. The thiourea-modified silica gel filter cake is rinsed with EtOAc (150 mL) and the rinse is returned to the reactor. If necessary, an activated carbon treatment may be implemented to remove color. The solution is passed through a polish filter to obtain a solution of 2,4,6-trifluoro-N-[6-(1-methylpiperidine-4-carbonyl)-2-pyridyl]benzamide.

The solution of 2,4,6-trifluoro-N-[6-(1-methylpiperidine-4-carbonyl)-2-pyridyl]benzamide is concentrated at 50° C. under reduced pressure to ~150 mL. EtOH (250 mL, denatured with toluene) is charged and the contents are concentrated at 50° C. under reduced pressure to ~150 mL. This is repeated for a total of 3 cycles to achieve adequate toluene removal before a final toluene charge to a total of 250 mL. The resulting toluene mixture is heated to 55° C. To a separate vessel is charged succinic acid (8.6 g, 73 mmol) and EtOH (200 mL, denatured with toluene). The contents of the vessel are stirred until complete dissolution of succinic acid is achieved. Approximately 30 mL of the succinic acid solution is transferred to the solution of 2,4,6-trifluoro-N-[6-(1-methylpiperidine-4-carbonyl)-2-pyridyl]benzamide and the resulting solution is stirred at 55° C. 2,4,6-trifluoro-N-[6-(1-methylpiperidine-4-carbonyl)-2-pyridyl]benzamide hemisuccinate is added as seed crystals either as a solid or a slurry in toluene denatured EtOH. The remainder of the succinic acid in toluene denatured EtOH solution is transferred to the reactor over 1.5 hr. The contents of the reactor are cooled to RT over 10 hours. The resulting slurry may be slurry milled to control particle size. If slurry milled, the contents of the reactor may undergo a series of thermal cycles via heating to 60° C. and cooling back to RT over 4 hr with stirring to further control particle size distribution. The slurry is filtered and rinsed with EtOH (100 mL, denatured with toluene) and dried at 40° C. under reduced pressure for 12 hr to provide the title compound (43.9 g, 73% yield). MS m/z 378 (M+H). The dried solids may then be jet milled for further particle size control.

Description of Drug Product Methods of Manufacture

In an embodiment lasmiditan prepared by the processes provided herein can further be prepared as certain useful drug product forms. In an embodiment such drug product forms are available as oval 50 and 100 mg, debossed, aqueous film-coated, immediate-release tablets. The 50 mg tablet is a light gray, oval tablet debossed with "4312" on one side and "L-50" on the other. The 100 mg tablet is light purple, oval tablet debossed with "4491" on one side and "L-100" on the other.

The following unit formula can be used in manufacturing lasmiditan tablets. Ingredient naming conventions are according to the USP.

TABLE 2

Unit Formula for Lasmiditan 50 mg and 100 mg Tablets

| Component | Quantity 50 mg | 100 mg | Description |
|---|---|---|---|
| Core Tablet - Intragranular Components | | | |
| Lasmiditan Hemisuccinate$^a$ | 57.824 | 115.65 | Active Ingredient |
| Lasmiditan Free Base | 50 | 100 | |

TABLE 2-continued

Unit Formula for Lasmiditan 50 mg and 100 mg Tablets

| Component | Quantity 50 mg | 100 mg | Description |
|---|---|---|---|
| Microcrystalline Cellulose[a] | 30.86 | 61.71 | Filler |
| Pregelatinized Starch | 7.500 | 15.00 | Binder |
| Croscarmellose Sodium | 5.630 | 11.26 | Disintegrant |
| Sodium Lauryl Sulfate, | 0.5600 | 1.120 | Wetting Agent |
| Purified Water[b] | — | — | Granulating Liquid |
| | (4.774)[c] | (9.548)[c] | |
| Core Tablet - Extragranular Components | | | |
| Croscarmellose Sodium | 7.880 | 15.76 | Disintegrant |
| Magnesium Stearate | 2.250 | 4.500 | Lubricant |
| Core Tablet Weight: | 117.3 | 234.5 | |
| Film Coating | | | |
| Color Mixture Gray | 3.519 | — | Colorant |
| Color Mixture Purple | — | 7.035 | Colorant |
| Purified Water[d] | — | — | Solvent |
| Total Tablet Weight: | 120.8 | 241.5 | |

Table 2 Notes:
[a] A salt conversion factor of 0.86469 is used to calculate the quantity of lasmiditan hemisuccinate. The quantity of microcrystalline cellulose may be adjusted accordingly to maintain target tablet weight.
[b] Purified Water is used in the granulation operation. The majority of the water is subsequently removed during the drying operation.
[c] A small quantity of residual water remains following the drying process, which may be in the form of free water or as water of hydration associated with drug substance.
[d] Purified water is used in the coating unit operation. The coating suspension is comprised of 20% w/w solids. Sufficient coating is sprayed to target a weight gain of 3%. This water is removed during the coating unit operation.

Tablet Manufacture:

Lasmiditan tablets are manufactured using a high shear wet granulation process which is described as follows. High Shear Wet Granulation: Sodium lauryl sulfate is passed through a security screen and added to purified water to form the granulating liquid. Lasmiditan drug substance and the excipients to be wet granulated (microcrystalline cellulose, pregelatinized starch, croscarmellose sodium) are passed through a security screen and combined in the granulator. The materials are mixed with the main impeller of the granulator prior to the addition of the granulating liquid. The powder blend is granulated in the granulator by adding the granulating liquid, while the powder is mixing. Upon completion of the liquid addition, the granulation is wet massed to facilitate liquid distribution. The granulation is coarsely sized by passing through a cone mill prior to drying.

Fluidized Bed Drying: The granulation is dried in a fluidized bed dryer until a moisture value of (50 mg and 100 mg: NMT 7%) is achieved, as measured by a gravimetric loss on drying method, or using a scientifically justified equivalent method. The dried granules are passed through a cone mill and added to a tumble bin.

Final Blend—Extragranular Powder Blend and Final Blend Lubrication: The extragranular croscarmellose sodium is passed through a security screen, and added to the dry milled granules in the tumble bin. The materials are tumble blended. The extragranular magnesium stearate is passed through a security screen, and added to the tumble bin. The materials are tumble blended.

Tablet Compaction: The blended granulation is compressed into tablets using a rotary compression machine. The compression parameters are selected at the start of a batch to achieve the target average (n=10) tablet weight of (50 mg: 111.4 mg-123.2 mg, 100 mg: 222.8-246.2 mg) and average (n=10) tablet breaking force of (50 mg: 4.1-13.7 kiloponds, 100 mg: 6.0-17.9 kiloponds). The average (n=10) core tablet weight, tablet breaking force, and tablet thickness are evaluated during start-up and throughout the compression unit operation. Tablet friability and tablet disintegration time are evaluated at the start-up of compression.

Film Coating of Core Tablets: The color mixture (gray for the 50 mg, and purple for the 100 mg) is passed through a security screen and mixed with purified water to form the coating suspension. The tablets are film-coated with the suspension utilizing spray guns in a perforated coating pan. The pan is rotated while the coating suspension is applied at a controlled rate with pneumatic atomization, and drying air is passed through the tablet bed to yield an acceptable exhaust temperature. Sufficient coating is sprayed to achieve the desired percent coating applied (50 mg and 100 mg: 2.0%-5.5%). The film-coated tablets are inspected for visual quality following the completion of coating step. The film-coated tablets are discharged into bulk storage containers and may be sorted (optional).

Container Closure System—Unit-Dose Blisters:

Lasmiditan tablets are provided in individual blister cavities formed from polychlorotrifluoroethylene (PCTFE)/polyvinylchloride (PVC) laminated film and sealed with aluminum foil laminate lidding material which contains a PVC-based heat seal coating.

Preparation and Description of 2,4,6-trifluoro-N-[6-(1-methylpiperidine-4-carbonyl)-2-pyridyl]benzamide acetate

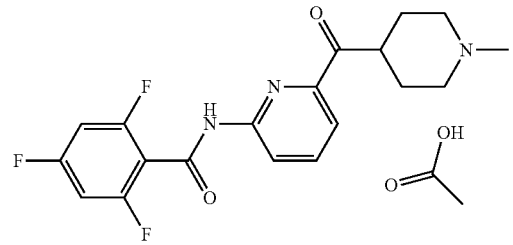

Preparation of 2,4,6-trifluoro-N-[6-(1-methylpiperidine-4-carbonyl)-2-pyridyl]benzamide acetate (also referred to as lasmiditan acetate) is performed by placing 2,4,6-trifluoro-N-[6-(1-methylpiperidine-4-carbonyl)-2-pyridyl]benzamide (541 mg, 1.6 mmol) in isopropyl acetate (5 mL) while stirring at 1000 rpm at room temperature. Acetic acid (100 μL) is added. A white solid precipitates out of solution after about two minutes of stirring. Stirring is shut off after 10 minutes, the white solid is collected by vacuum filtration on Whatman paper and dried in place under air stream for 10 minutes to yield the title compound (650 mg, 92% yield).

Counterion stoichiometry is measured by nuclear magnetic resonance using an Agilent 400-MHz spectrometer. A sample solution is prepared by dissolving the prepared 2,4,6-trifluoro-N-[6-(1-methylpiperidine-4-carbonyl)-2-pyridyl]benzamide acetate (7.715 mg) and maleic acid (5.949 mg), used as standard for other measurements, in DMSO-$d_6$ (approximately 0.75 mL). A $^{13}$C-decoupled $^1$H spectrum of the sample from 0-12 ppm is acquired using the following parameters: 90-degree excitation pulse, 64 scans, 25-second relaxation delay, and 4.5-second acquisition time. The resonances for acetate at approximately 1.9 ppm (3H) and for 2,4,6-trifluoro-N-[6-(1-methylpiperidine-4-carbonyl)-2-pyridyl]benzamide at approximately 7.8 ppm (1H) are integrated to obtain areas of 29094 and 9508, respectively. The molar ratio of acetate to 2,4,6-trifluoro-N-[6-(1-methylpiperidine-4-carbonyl)-2-pyridyl]benzamide is calculated by taking the ratio of these areas, accounting for the difference in proton count for resonance, yielding an observed molar ratio of 29094/(3×9508)=1.02 acetate: 2,4,6-trifluoro-N-[6-(1-methylpiperidine-4-carbonyl)-2-pyridyl]benzamide. See for example FIG. 1 which shows an $^1$H NMR spectrum (400 MHz, DMSO-$d_6$) of lasmiditan acetate containing maleic acid (internal standard). This result provides experimental evidence that the prepared example of 2,4,6-trifluoro-N-[6-(1-methylpiperidine-4-carbonyl)-2-pyridyl]benzamide acetate is a mono-acetate salt.

X-Ray Powder Diffraction (XRPD) of 2,4,6-trifluoro-N-[6-(1-methylpiperidine-4-carbonyl)-2-pyridyl]benzamide acetate The XRPD patterns of 2,4,6-trifluoro-N-[6-(1-methylpiperidine-4-carbonyl)-2-pyridyl]benzamide acetate crystalline solids are obtained on a Bruker D4 Endeavor X-ray powder diffractometer, equipped with a CuKα source and a Vantec detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

A prepared sample of crystalline acetate salt is characterized by an XRPD pattern using CuKa radiation as having diffraction peaks (2-theta values) as described in Table 3 below, and in particular having peaks at 26.2 in combination with one or more of the peaks selected from the group consisting of 20.4, 14.0, and 17.9; with a tolerance for the diffraction angles of 0.2 degrees.

TABLE 3

X-ray powder diffraction peaks of crystalline 2,4,6-trifluoro-N-[6-(1-methylpiperidine-4-carbonyl)-2-pyridyl]benzamide acetate salt

| | 2,4,6-trifluoro-N-[6-(1-methylpiperidine-4-carbonyl)-2-pyridyl]benzamide acetate | |
|---|---|---|
| Peak | Angle (° 2-Theta) +/− 0.2° | Relative Intensity (% of most intense peak) |
| 1 | 8.2 | 40.4% |
| 2 | 9.7 | 29.6% |
| 3 | 12.0 | 35.8% |
| 4 | 14.0 | 65.0% |
| 5 | 16.9 | 43.8% |
| 6 | 17.9 | 63.2% |
| 7 | 20.4 | 70.5% |
| 8 | 23.3 | 30.6% |
| 9 | 24.3 | 43.9% |
| 10 | 26.2 | 100.0% |

Solubility of Lasmiditan Acetate and Use For Formulations For Subcutaneous Injection Lasmiditan acetate was discovered to be surprisingly superior to many alternative salt forms for the preparation of a subcutaneous formulation to deliver a dose of lasmiditan in minimal volume in near-physiological fluid. Lasmiditan acetate was discovered to enable a desired dose target of about 50 mg in the minimal volume of less than or equal to about 1 mL, while at the same time achieving a desired target pH being close to neutral, and in addition being relatively isotonic and physically and chemically stable. Using lasmiditan hemisuccinate it was experimentally determined that achieving >50 mg/mL solubility, at close to neutral pH, was difficult without using co-solvents. For solubility determinations 10 mmol buffer is made with a respective acid and salt, and pH is adjusted by changing the acid/salt ratio. Excess solid is equilibrated at RT overnight, and solution concentration is analyzed by HPLC and solid was characterized by XRPD. In contrast, for lasmiditan acetate it was discovered that solubility of >50 mg/mL can be achieved, at close to neutral pH, without adjusting the pH.

TABLE 4

Solubility of Lasmiditan Acetate in acetate, citrate, or phosphate buffer. A 10 mmol buffer is made with respective acid and salt, and pH is adjusted by changing acid/salt ratio. All added solute went into solution to form a viscous solution.

| Buffer media | Solid form | pH (before) | pH (after) | Solubility (Free Base eq. mg/mL) |
|---|---|---|---|---|
| Acetate | Lasmiditan Acetate | 3.69 | 6.25 | >441 |
| Acetate | Lasmiditan Acetate | 4.05 | 6.41 | >430 |
| Acetate | Lasmiditan Acetate | 4.4 | 6.31 | >412 |
| Acetate | Lasmiditan Acetate | 5.09 | 6.50 | >430 |
| Acetate | Lasmiditan Acetate | 5.71 | 6.56 | >486 |
| Citrate | Lasmiditan Acetate | 2.5 | 5.60 | >300 |
| Citrate | Lasmiditan Acetate | 3.84 | 5.72 | >300 |
| Citrate | Lasmiditan Acetate | 4.99 | 6.23 | >300 |
| Citrate | Lasmiditan Acetate | 5.96 | 6.24 | >300 |
| Phosphate | Lasmiditan Acetate | 8.24 | 6.42 | >300 |

It was discovered that lasmiditan acetate surprisingly demonstrates a highly advantageous combination of pharmaceutical properties. Lasmiditan acetate enables the desired solubility to provide high concentration formulations having a less than or equal to about 1 mL dose volume, for the desired unit doses, which is critical for clinical applications such as use in available autoinjector devices. In addition, dissolution of lasmiditan acetate at 50 mg/mL results in close to neutral pH (pH approximately 6.8), is isotonic, and stable for at least 2 months. Lasmiditan acetate demonstrates significantly higher solubility than lasmiditan hemisuccinate salt with a desirable pH profile and enables delivery of the required unit doses in volumes of about 1 mL or less.

These results indicate that lasmiditan acetate enables a surprisingly high concentration aqueous solution of lasmiditan, with useful pharmaceutical properties for clinical parenteral administration, such as subcutaneous injection. The pharmacological activities of lasmiditan are well-established (Curto, M. et al. *Profiling lasmiditan as a treatment option for migraine*. Expert Opinion on Pharmacotherapy (2020), Volume 21, Issue 2, pages 147-153). Preferably subcutaneous injection is administered by prefilled syringe or autoinjector, employing devices known to the skilled artisan (See e.g. Stauffer V L, et al., *Comparison between prefilled syringe and autoinjector devices on patient-reported experiences and pharmacokinetics in galcanezumab studies*, Patient Prefer Adherence. (2018) 12:1785-1795, and van den Bemt B J F, et al., *A portfolio of biologic self-injection devices in rheumatology: how patient involvement in device design can improve treatment experience*, Drug Deliv. (2019), 26(1):384-392). These formats provide for a fixed dose, with no measurement by patient, providing dose accuracy and safety, while enabling self-reliance by the patient. Use of the lasmiditan acetate salt for acute treatment of migraine attack in formats such as autoinjectors provide improved tools for institutional patients, such as those in hospital emergency settings where patient use of tablets is impaired by the migraine attack and associated nausea and vomiting, and the patients and/or providers prefer an improved injectable form of lasmiditan. Lasmiditan acetate parenteral formulations are expected to provide immediate release, enabling rapid time to onset of action, and may preferably allow for shorter time to efficacy relative to oral dose forms when used on demand at the outset of a migraine attack.

Providing lasmiditan formulations for injection at neutral and physiological pH (approximately 6.0-7.5), and isotonic with physiological fluid (e.g. 280 to 300 mosm/kg), is clinically highly desirable and considered to minimize the likelihood of pain on injection, and/or tissue irritation, for example. Achieving injection volumes of about 1 ml or less enable the use of available injector technologies, such as autoinjectors, and provide for improved injection and delivery experiences for patients with regard to injection time, and/or pain on injection, for example. Enabling the use of pre-filled syringes, pens, and/or autoinjector technologies is clinically significant for migraine patients as these devices provide an ease of use during migraine attacks when patients are often under duress at the time of product use. Further, enabling the use of pre-filled syringes, pens, and/or autoinjector technologies is clinically significant because they provide portable access to medication, at any time, which is easily accessible in the course of daily living, where a migraine attack can occur at any time.

The following unit formula can be used in manufacturing lasmiditan solution for injection.

TABLE 5

Unit Formula for Lasmiditan 50 mg Solution in an Autoinjector

| Component | Quantity (mg/autoinjector) | Description |
|---|---|---|
| Lasmiditan | 50.00 | Active Ingredient |
| Lasmiditan Acetate | 57.96 | |
| Acetic Acid Solution (10%) | Sufficient to Adjust pH if needed | pH Adjustment |
| Sodium Hydroxide Solution (10%) | Sufficient to Adjust pH if needed | pH Adjustment |
| Water for Injection | q.s. to 1 mL | Solvent |

We claim:

1. An immediate-release tablet, wherein the tablet comprises:
   (a) from 50 mg to 100 mg free base equivalent of 2,4,6-trifluoro-N-[6-(1-methyl-piperidine-4-carbonyl)-pyridin-2-yl]-benzamide hemisuccinate;
   (b) from 30.86 mg to 61.71 mg of microcrystalline cellulose;
   (c) from 7.5 mg to 15.00 mg of pregelatinized starch;
   (d) from 0.56 mg to 1.12 mg of sodium lauryl sulfate;
   (e) from 5.63 mg to 40.53 mg of croscarmellose sodium;
   (f) from 2.25 mg to 4.50 mg of magnesium stearate; and
   (g) from 3.519 mg to 7.035 mg of the film coating.

2. The immediate release tablet of claim 1, wherein the tablet comprises:
   (a) 50 mg free base equivalent of 2,4,6-trifluoro-N-[6-(1-methyl-piperidine-4-carbonyl)-pyridin-2-yl]-benzamide hemisuccinate;
   (b) 30.86 mg of microcrystalline cellulose;
   (c) 7.5 mg of pregelatinized starch;
   (d) 0.56 mg of sodium lauryl sulfate;
   (e) 13.51 mg of croscarmellose sodium;
   (f) 2.25 mg of magnesium stearate; and
   (g) 3.519 mg of the film coating.

3. The immediate-release tablet of claim 1, wherein the tablet comprises:
   (a) 100 mg free base equivalent of 2,4,6-trifluoro-N-[6-(1-methyl-piperidine-4-carbonyl)-pyridin-2-yl]-benzamide hemisuccinate;
   (b) 61.71 mg of microcrystalline cellulose;
   (c) 15.00 mg of pregelatinized starch;
   (d) 1.12 mg of sodium lauryl sulfate;
   (e) 40.53 mg of croscarmellose sodium;
   (f) 4.50 mg of magnesium stearate; and
   (g) 7.035 mg of the film coating.

4. The immediate-release tablet of claim 1, wherein the tablet is provided in a unit-dose blister.

* * * * *

UNITED STATES PATENT AND TRADEMARK OFFICE
CERTIFICATE OF CORRECTION

PATENT NO. : 12,071,423 B2
APPLICATION NO. : 18/134747
DATED : August 27, 2024
INVENTOR(S) : Aktham Aburub et al.

Page 1 of 1

It is certified that error appears in the above-identified patent and that said Letters Patent is hereby corrected as shown below:

In the Claims

Column 34, Line 32, Claim 2 delete "immediate release" and insert --immediate-release--

Signed and Sealed this
Thirty-first Day of December, 2024

Derrick Brent
*Acting Director of the United States Patent and Trademark Office*